US011090001B2

(12) United States Patent
Stevens et al.

(10) Patent No.: US 11,090,001 B2
(45) Date of Patent: Aug. 17, 2021

(54) MONITORING DEVICE FOR DETECTING WETNESS IN A GARMENT

(71) Applicant: RSC Associates, Inc., Bowling Green, OH (US)

(72) Inventors: Thomas Reed Stevens, Palo Alto, CA (US); Suguru Nishioka, San Francisco, CA (US); Ivan J. Goering, Palo Alto, CA (US)

(73) Assignee: RSC ASSOCIATES, INC., Bowling Green, OH (US)

( * ) Notice: Subject to any disclaimer, the term of this patent is extended or adjusted under 35 U.S.C. 154(b) by 364 days.

(21) Appl. No.: 16/014,723

(22) Filed: Jun. 21, 2018

(65) Prior Publication Data

US 2019/0388029 A1     Dec. 26, 2019

(51) Int. Cl.
| | |
|---|---|
| *A61F 13/42* | (2006.01) |
| *A61B 5/20* | (2006.01) |
| *A61B 5/00* | (2006.01) |
| *A61F 13/44* | (2006.01) |
| *A61F 13/84* | (2006.01) |

(52) U.S. Cl.
CPC ............ *A61B 5/6808* (2013.01); *A61B 5/202* (2013.01); *A61F 13/42* (2013.01); *A61F 13/44* (2013.01); *A61B 2503/08* (2013.01); *A61F 2013/424* (2013.01); *A61F 2013/8473* (2013.01)

(58) Field of Classification Search
CPC .... A61F 13/42; A61F 13/44; A61F 2013/424; A61F 2013/425; A61F 2013/8473; A61F 6/206; A61B 5/202; A61B 5/6808; A61B 2017/2808; A44B 11/06; A44B 11/10;

(Continued)

(56) References Cited

U.S. PATENT DOCUMENTS

| | | | | |
|---|---|---|---|---|
| 6,573,837 B2 * | 6/2003 | Bluteau | ................... | A61F 13/42 340/573.5 |
| 6,745,924 B2 * | 6/2004 | Woodworth | ......... | A47G 25/483 223/87 |

(Continued)

FOREIGN PATENT DOCUMENTS

| | | |
|---|---|---|
| WO | 2016/064378 A1 | 4/2016 |
| WO | 2018/098300 A1 | 5/2018 |

OTHER PUBLICATIONS

PCT, U.S. Patent and Trademark Office (ISA/US), International Search Report, International Application No. PCT/US2019/038151, 2 pages (dated Sep. 11, 2019).

(Continued)

*Primary Examiner* — Catharine L Anderson
*Assistant Examiner* — Lynne Anderson
(74) *Attorney, Agent, or Firm* — Thompson Hine LLP

(57) ABSTRACT

A monitoring device for detecting wetness in a garment is disclosed. The monitoring device of the present disclosure includes a locking mechanism that slides back and forth relative to a clip that is removably attachable to a garment between a first position in which the locking mechanism locks the clip in a closed position and a second position in which the clip is in an open position. As the locking mechanism transitions from the first position to the second position, the locking mechanism opens the clip. Advantageously, the monitoring device of the present disclosure allows a caregiver to align and secure the monitoring device to a garment using only one hand.

23 Claims, 19 Drawing Sheets

(58) Field of Classification Search
CPC .............. A44B 11/14; A61M 2025/024; Y10T 24/4453; Y10T 24/44692; Y10T 24/44744
USPC ................................. 24/304; 223/90, 94, 96
See application file for complete search history.

(56) References Cited

U.S. PATENT DOCUMENTS

| | | | |
|---|---|---|---|
| 7,250,547 B1* | 7/2007 | Hofmeister | A61F 13/42 340/573.5 |
| 7,477,156 B2* | 1/2009 | Long | A61F 13/42 340/573.5 |
| 8,245,366 B2* | 8/2012 | Morejon | A47D 15/008 24/457 |
| 8,274,393 B2* | 9/2012 | Ales | A61F 13/42 340/604 |
| 8,628,506 B2* | 1/2014 | Ales | A61F 13/42 604/318 |
| 10,258,512 B2* | 4/2019 | Vartiainen | A61F 13/42 |
| 2006/0058745 A1* | 3/2006 | Pires | A61F 13/42 604/361 |
| 2009/0144943 A1 | 6/2009 | Arranz Del Rosal et al. | |
| 2010/0271212 A1* | 10/2010 | Page | A61B 5/4216 340/573.1 |
| 2016/0002514 A1 | 1/2016 | Determan et al. | |
| 2019/0287678 A1* | 9/2019 | Stevens | G16H 40/67 |

OTHER PUBLICATIONS

PCT, U.S. Patent and Trademark Office (ISA/US), Written Opinion of the International Searching Authority, International Application No. PCT/US2019/038151, 6 pages (dated Sep. 11, 2019).

PCT, The International Bureau of WIPO, International Preliminary Report on Patentability, International Application No. PCT/US2019/038151, 7 pages (dated Dec. 22, 2020).

* cited by examiner

MONITORING DEVICE FOR DETECTING WETNESS IN A GARMENT

BACKGROUND OF THE INVENTION

1. Field of the Disclosure

The present disclosure relates generally to a monitoring device. More particularly, the present disclosure relates to a monitoring device for detecting wetness in a garment.

2. Description of the Related Art

Incontinence in patient care environment is a growing problem in patient care and home care of elderly patients. Urinary incontinence is the involuntary leakage of urine. Many patients have the inability to hold urine in their bladder because voluntary control over the urinary sphincter is either lost or weakened. Urinary incontinence is a much more common problem than most people realize.

It is common for nursing homes and hospitals to lack the staff and financial resources to provide residents with sufficiently frequent toileting assistance (including prompted voiding). Use of special undergarments and absorbent pads or catheterization is the usual practice.

Urinary incontinence (UI) and fecal incontinence (FI) are commonly encountered in nursing home residents and are associated with significant morbidity and utilization of health care resources. Urinary incontinence has been estimated to affect between 50% and 65% of nursing home residents, and a majority of these residents also have FI. UI is also prevalent in the at-home aging population and is a leading factor in senior isolation and eventual institutionalization in a care facility.

There are several key activities of daily living (ADL) that are indicative of quality of life and safety in an aging population including: toileting, sleep, medication, and nutrition. Incontinence is a critical ADL deficit that negatively impacts all aspects of autonomy, health, and overall well-being. It is a leading cause of seniors' loss of independence and requiring professional care. The demand for improved incontinence solutions exists, in ever increasing levels of severity, at every stage in elder care from family caregiving through to acute care hospitalization, with the highest utilization rates occurring in long-term living facilities. Sleep quality is another key indicator that augments and inter-relates with incontinence.

Elderly people constitute a large and growing portion of the world's population. Many of them are physically and mentally vulnerable and need continuous support for their health and well-being. There is a growing trend that these elderly people are placed in an ambient assisted living environment (AAL) with an aim to receive better care and support. However, much less attention has been directed toward understanding incontinence needs of elderly people, which is an important factor relevant to their physical and mental health and joyful living.

One in three adult women live with some level of urinary incontinence. Nearly 40% (19 million) of all seniors and over 60% (15 million) of female seniors live with incontinence, with increasing prevalence and severity as age increases. Suboptimal incontinence care leads to degenerative skin health, an increased risk of falls as patients unsuccessfully attempt to self-toilet, and critical declines in mental health. As a result, it is the leading cause of senior isolation and institutionalization. Clinical nurses and the research community agree that there is clear correlation between incontinence and pressure ulcers and urinary tract infections (UTIs). UTIs and pressure wounds are directly linked to increased negative outcomes.

The cost to treat pressure ulcers can be very expensive and is estimated between $9.1-11.6 billion per year, affecting over 2.5 million patients. Approximately 60,000 people die each year as a direct result of a pressure ulcer. Keeping the skin free from exposure to urine and stool is very important in treating pressure ulcers and bedsores. Similarly, UTIs are rampant as well, as a result of over-catheterization, totaling over $340 million per year and with at least 13,000 deaths a year are associated with UTIs. Increased costs and negative outcomes with UTIs are likely as the patient population grows older.

For enterprise businesses, incontinence is a significant issue. For caregivers, such as acute care hospitals, incontinence is a contributor to revenue loss and a key source of family dissatisfaction with institutional providers. Nearly $4 billion is spent on adult non-woven absorbency products in the US ($9 billion globally), and the segment is growing as the Baby Boomers continue to age and live longer than their predecessors.

It is known that the complications of urinary incontinence are increasingly and rapidly expanding as the world's population is aging longer with each New Year. Many elderly people encounter skin problems, but an elderly person with urinary incontinence is even more likely to have skin sores, rashes, and infections because the skin is wet or damp. This is bad for wound healing and also promotes fungal infections. Urinary tract infections are a significant risk, and long-term use of urinary catheters also significantly increases the risk of infection.

The problem has been addressed in part by providing pads that are manually replaced when the nurse is visiting a room. The amount of times a product needs changed depends in part on how absorbent the pad, diaper, or pull-up is and the severity of the incontinence. Generally, it is best to change a product as soon as soiling occurs. This will reduce the risk of skin breakdown and infections caused by a lack of air flow, moist conditions, and long exposure to urine and fecal matter.

With each change, it is important to thoroughly clean the diaper area to reduce infections. After changing, it is important to properly dispose of soiled incontinence products.

Disposable briefs are more commonly known as adult diapers. Adult diapers are often used for heavy incontinence, nighttime wetting, and those who need help getting to the bathroom.

Therefore, there is a need to provide methods and an apparatus for improved incontinence sensing. Thus, there remains a considerable need for devices with improved incontinence sensing and systems that can quickly and accurately address a patient with a wet pad.

SUMMARY OF THE INVENTION

The present disclosure is directed to a monitoring device for detecting wetness in a garment. The monitoring device of the present disclosure includes a locking mechanism that slides back and forth relative to a clip that is removably attachable to a garment between a first position in which the locking mechanism locks the clip in a closed position and a second position in which the clip is in an open position. As the locking mechanism transitions from the first position to the second position, the locking mechanism opens the clip. Advantageously, the monitoring device of the present disclosure allows a caregiver to align and secure the monitoring device to a garment using only one hand.

In accordance with an embodiment of the present invention, a monitoring device for detecting wetness in a garment includes a clip removably attachable to the garment; and a locking mechanism movably connected to the clip, the locking mechanism transitionable between a first position in which the locking mechanism locks the clip in a closed position and a second position in which the clip is in an open position.

In one configuration, the locking mechanism slides back and forth relative to the clip between the first position and the second position. In another configuration, as the locking mechanism transitions from the first position to the second position, the locking mechanism opens the clip. In yet another configuration, the clip comprises a top portion and a bottom portion. In one configuration, the bottom portion of the clip includes a resilient member transitionable between a deformed position and an undeformed position. In another configuration, with the clip in the closed position, the resilient member is in the deformed position, and with the clip in the open position, the resilient member is in the undeformed position. In yet another configuration, with the locking mechanism in the second position, the clip is locked in the open position by the resilient member in the undeformed position exerting a force on the top portion of the clip. In one configuration, the top portion of the clip includes a rail and the locking mechanism includes a protrusion within the rail, wherein the rail guides movement of the locking mechanism relative to the clip between the first position and the second position. In another configuration, as the locking mechanism transitions from the first position to the second position, the protrusion within the rail exerts a force on the top portion of the clip, such that the locking mechanism opens the clip. In yet another configuration, the locking mechanism comprises a top part, a side part, and a bottom part. In one configuration, the top part, the side part, and the bottom part form a generally J-shape. In another configuration, the top part of the locking mechanism includes a protruding rib and the top portion of the clip defines a groove, and with the locking mechanism in the first position, the protruding rib locks within the groove. In yet another configuration, the bottom part of the locking mechanism includes a link movably connected to the bottom part of the locking mechanism and the bottom portion of the clip, and with the locking mechanism in the second position, the link locks the locking mechanism relative to the clip so that movement of the locking mechanism relative to the clip is prevented. In one configuration, the link comprises a detent system. In another configuration, the clip comprises an elastomeric portion, and with the clip in the closed position and the clip attached to the garment, the elastomeric portion grips the garment. In yet another configuration, with the clip in the open position, an opening angle between the top portion and the bottom portion is 35° or less. In one configuration, the locking mechanism comprises a polymer component molded over a metal component. In another configuration, the clip further comprises a sensor configured to determine moisture data associated with moisture in the garment; and a transmitter configured to connect to the sensor and transmit the moisture data to a computer system comprising one or more processors. In yet another configuration, the clip further comprises a printed circuit board; and a plurality of pins in communication with the printed circuit board, a portion of the plurality of pins extending through a portion of the clip, wherein, with the clip attached to the garment, the printed circuit board is in communication with the garment via the plurality of pins.

In accordance with another embodiment of the present invention, a monitoring system includes a monitoring device for detecting wetness in a garment, comprising: a clip; and a locking mechanism movably connected to the clip, the locking mechanism transitionable between a first position in which the locking mechanism locks the clip in a closed position and a second position in which the clip is in an open position; a first garment; and a second garment, wherein the clip of the monitoring device is removably attachable to the first garment and the second garment.

In one configuration, the monitoring device is reusable and the first garment and the second garment are disposable. In another configuration, the locking mechanism slides back and forth relative to the clip between the first position and the second position. In yet another configuration, as the locking mechanism transitions from the first position to the second position, the locking mechanism opens the clip.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
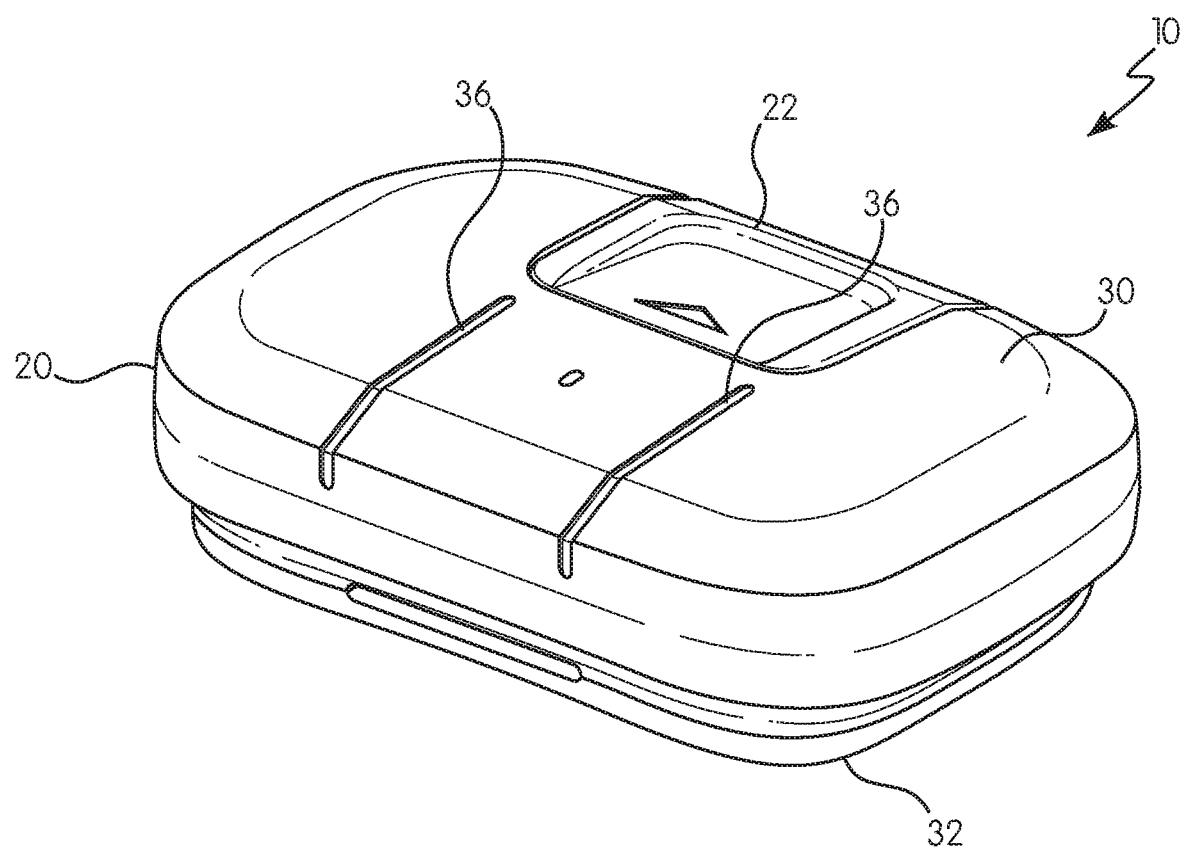
FIG. 1 is a perspective view of a monitoring device with a locking mechanism in a first position in accordance with an embodiment of the present invention.
Figure 2:
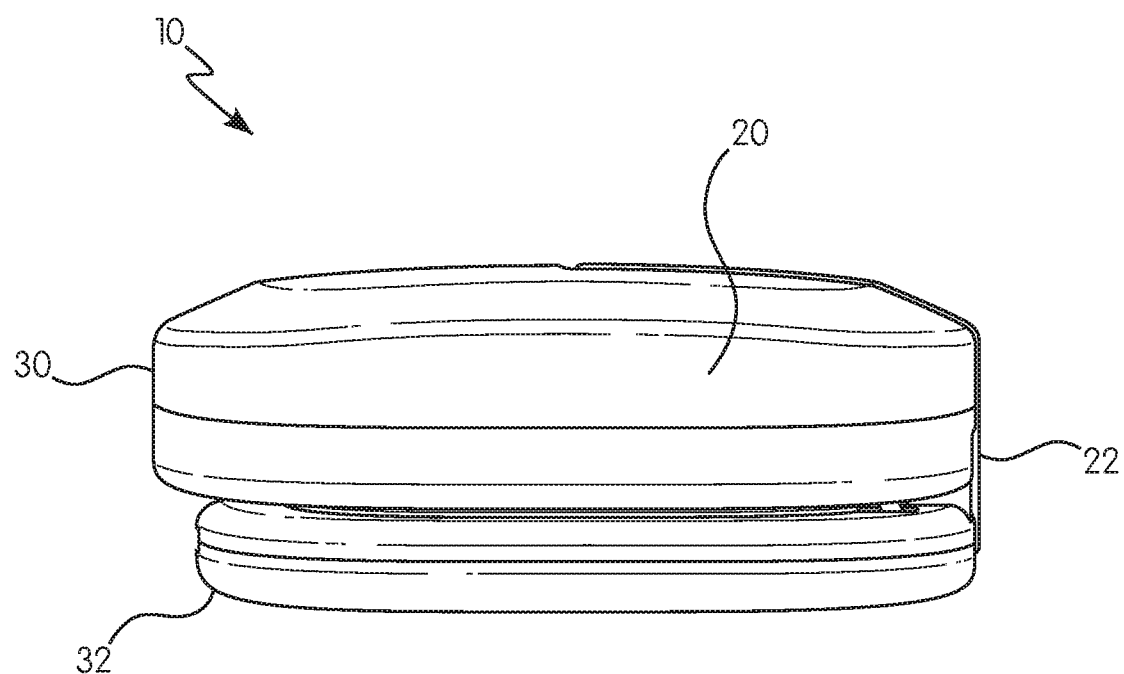
FIG. 2 is a side perspective view of a monitoring device with a locking mechanism in a first position in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present disclosure is directed to a monitoring device for detecting wetness in a garment. The monitoring device of the present disclosure includes a locking mechanism that slides back and forth relative to a clip that is removably attachable to a garment between a first position in which the locking mechanism locks the clip in a closed position and a second position in which the clip is in an open position. As the locking mechanism transitions from the first position to the second position, the locking mechanism opens the clip. Advantageously, the monitoring device of the present disclosure allows a caregiver to align and secure the monitoring device to a garment using only one hand.

Figure 3:
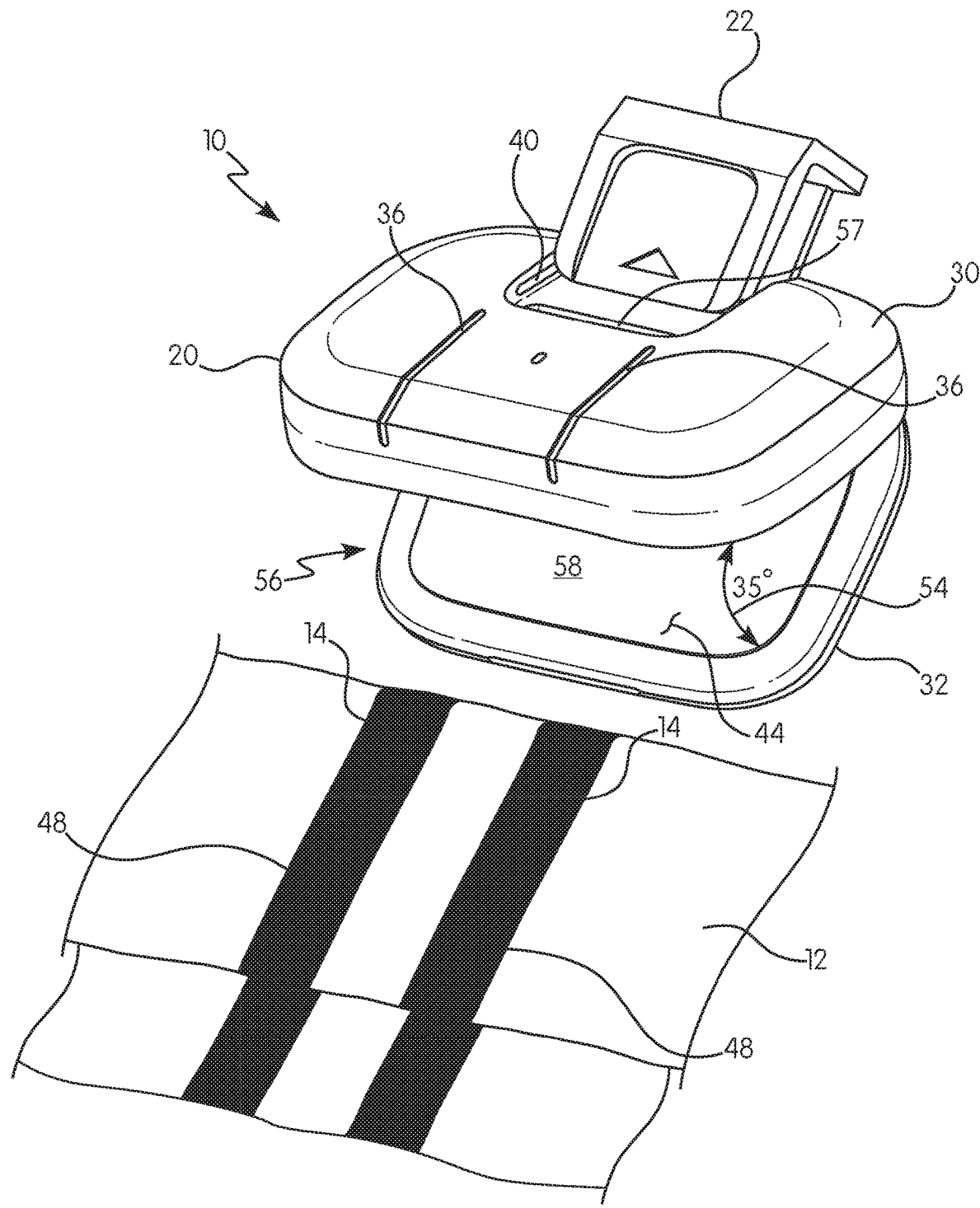
FIG. 3 is a perspective view of a monitoring device with a locking mechanism in a second position and the monitoring device aligned with a garment in accordance with an embodiment of the present invention.
Figure 7:
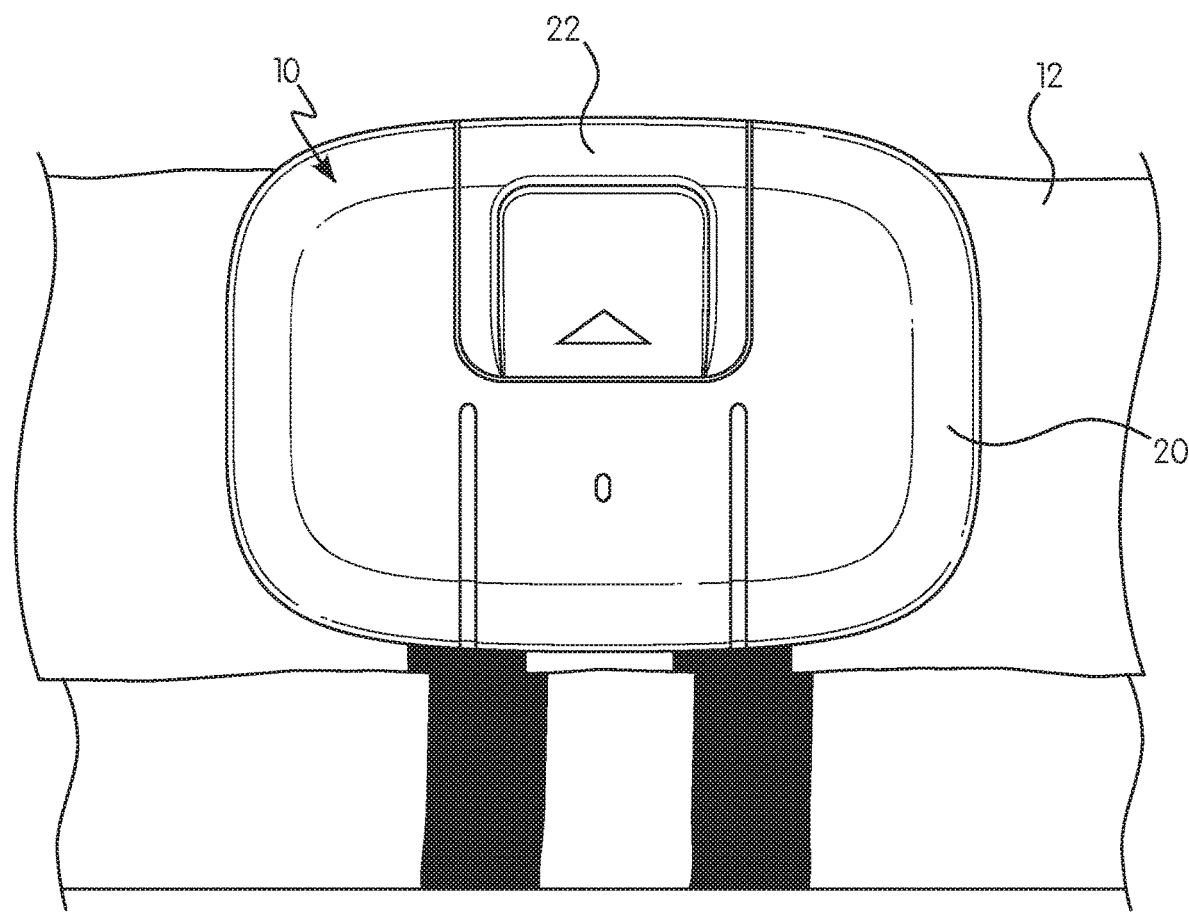
FIG. 7 is a perspective view of a monitoring device with a locking mechanism in a first position and the monitoring device attached to a garment in accordance with an embodiment of the present invention.
Figure 8:
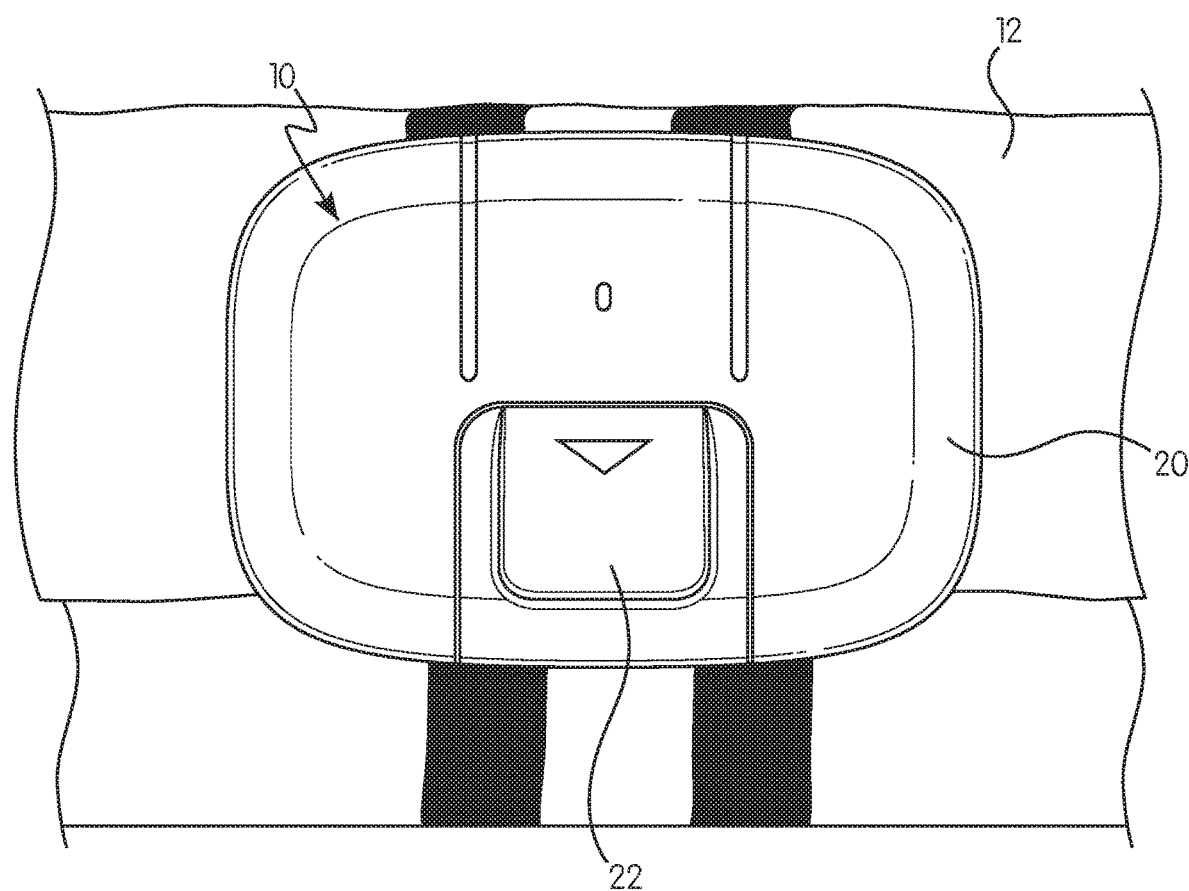
FIG. 8 is a perspective view of a monitoring device with a locking mechanism in a first position and the monitoring device attached to a garment in accordance with another embodiment of the present invention.

Referring to FIGS. 1-5 and 9-10, in an exemplary embodiment, a monitoring device 10 (e.g., a monitoring assembly, a housing assembly, etc.) for detecting wetness in a garment 12 (FIGS. 3 and 6-8) includes a clip 20 and a locking mechanism 22 (e.g., a latch, switch, lock, etc.). The clip 20 and locking mechanism 22 provide a mechanism for removably attaching the monitoring device 10 to a garment 12 as shown in FIGS. 3 and 7-8. The monitoring device 10 of the present disclosure is compatible with any type of undergarment such as, for example, pads, briefs, diapers, pull-ups, or other wearable garments.

Referring to FIGS. 1-5, the locking mechanism 22 is movably connected to the clip 20. In an exemplary embodiment, the locking mechanism 22 is transitionable between a first position (FIGS. 1-2 and 7-8) in which the locking mechanism 22 locks the clip 20 in a closed position and a second position (FIGS. 3-5) in which the clip 20 is in an open position.

Referring to FIGS. 1-5 and 9-10, in one exemplary embodiment, the clip 20 generally includes a top portion 30, a bottom portion 32, a hinge portion 33, a resilient member 34, guide lines 36, fasteners 38, rails 40 (FIG. 5), a link or first detent portion 42 (FIGS. 15 and 16), an elastomeric portion 44, and a printed circuit board 46 including a transmitter 50 (e.g., circuit board, etc.), and pins 52. In some non-limiting embodiments, sensors 48 may be placed inside a wearable unit, e.g., the garment 12, and may take the shape of the wearable unit. For example, in one exemplary embodiment, a sensor 48 and/or sensor pad may be attached to an interior of a garment 12. In some non-limiting embodiments, sensors may also be included (e.g., extend into, etc.) as part of the monitoring device 10.

In some non-limiting embodiments, the top portion 30 and the bottom portion 32 of the clip 20 are transitionable between a closed position (FIGS. 1-2 and 7-8) in which the clip 20 is securely attached to a garment 12 (FIGS. 3 and 7-8) and an open position (FIGS. 3-5) in which the top portion 30 is spaced away from the bottom portion 32. In the open position, an opening 56 is created between the top portion 30 and the bottom portion 32.

Figure 4:
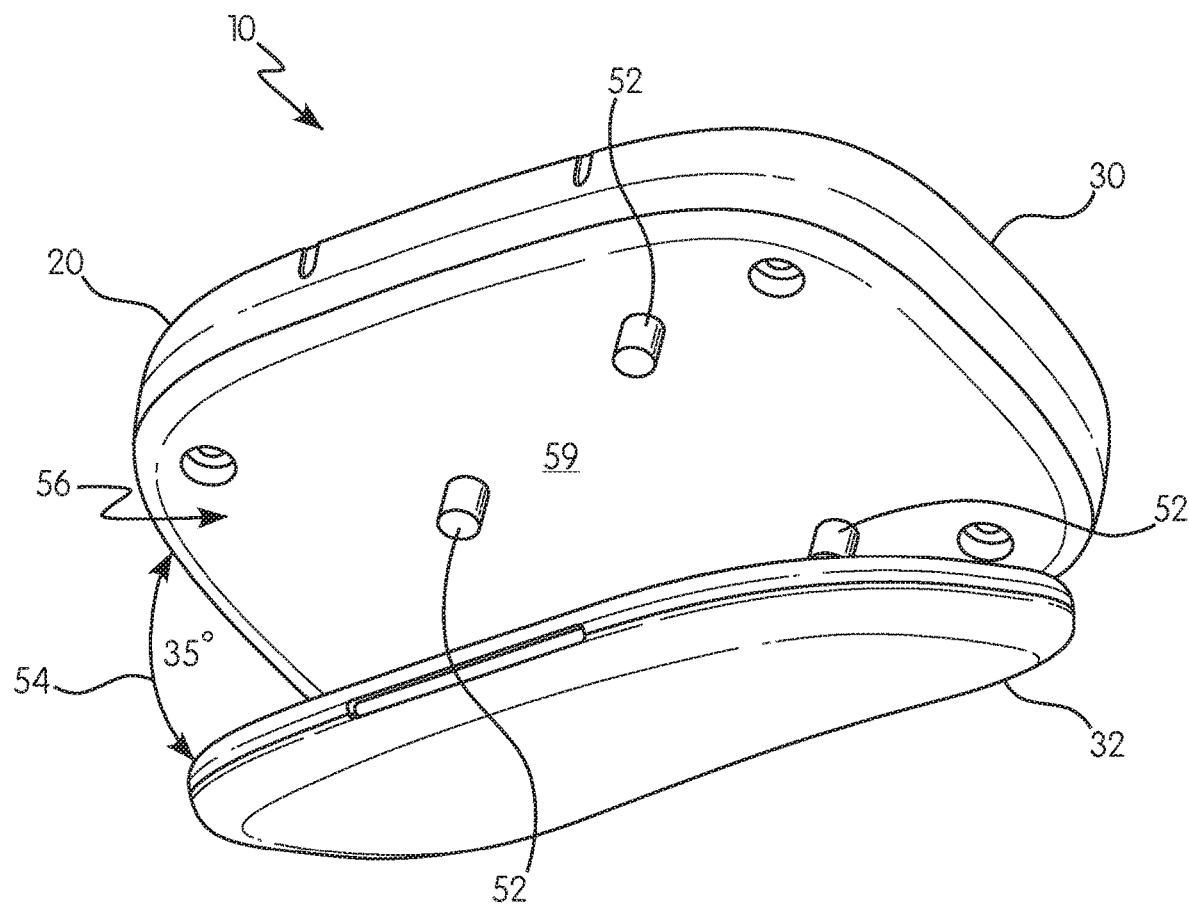
FIG. 4 is a perspective view of a monitoring device with a locking mechanism in a second position in accordance with an embodiment of the present invention.
Figure 5:
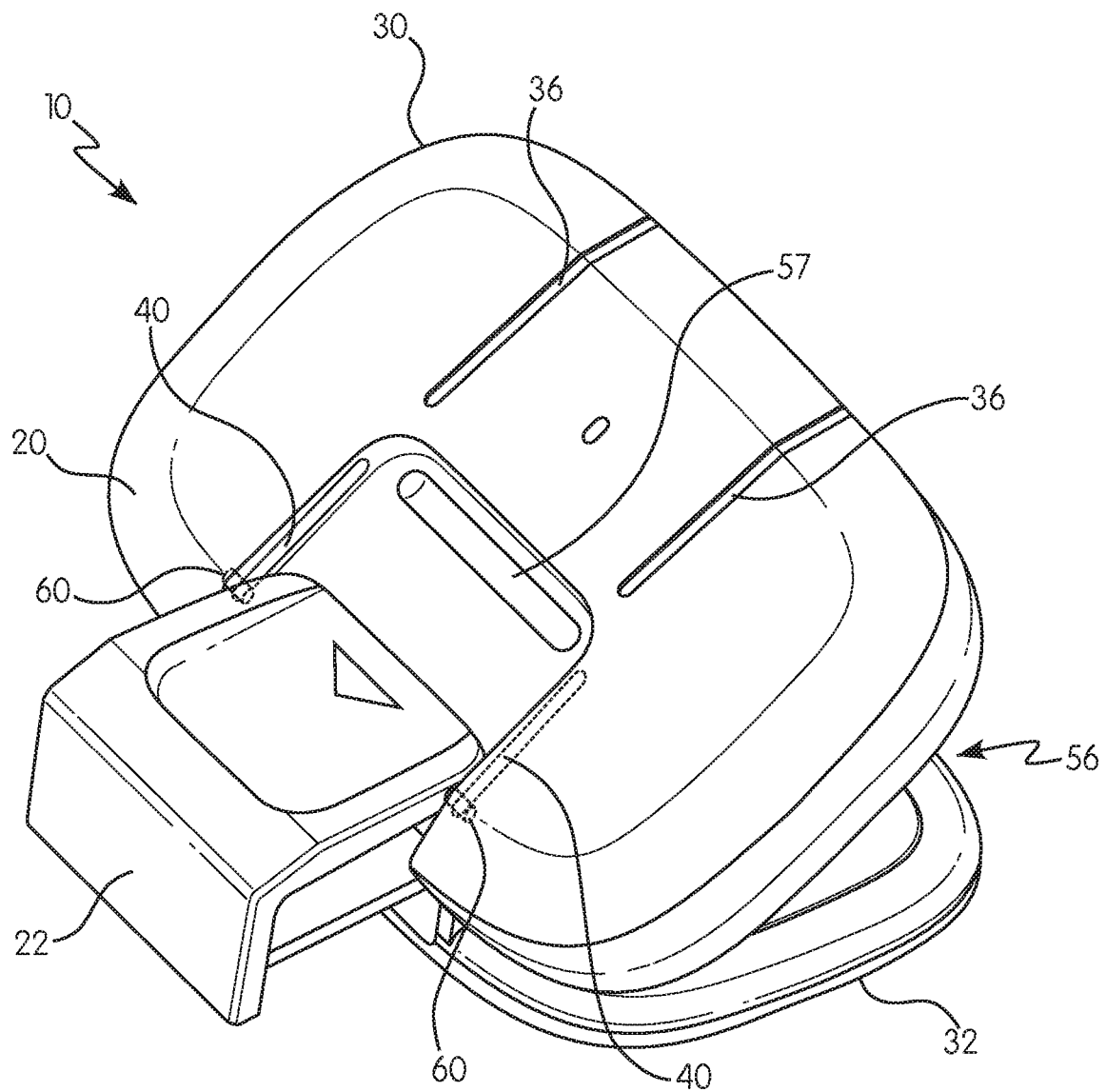
FIG. 5 is a perspective view of a monitoring device with a locking mechanism in a second position in accordance with another embodiment of the present invention.
Figure 6:
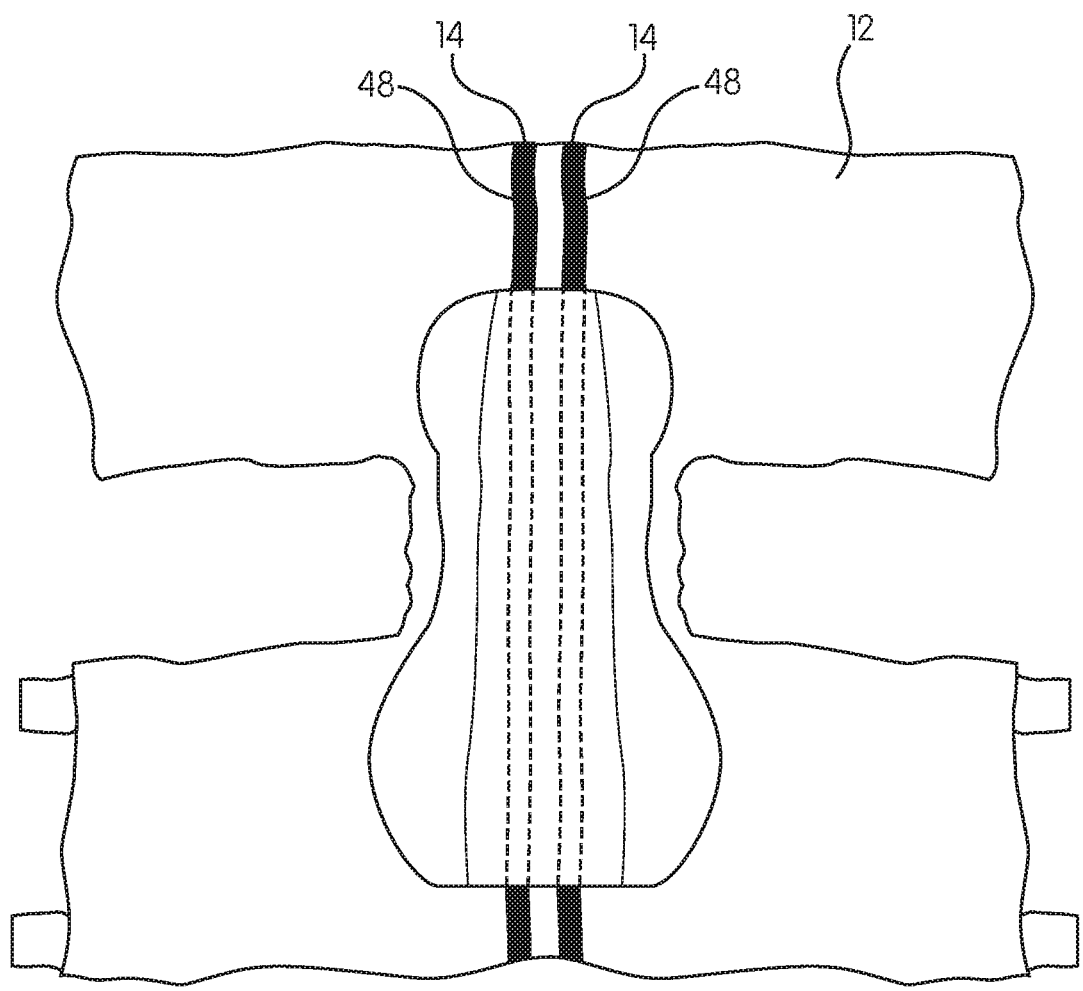
FIG. 6 is an elevation view of a garment in accordance with an embodiment of the present invention.

In some non-limiting embodiments, the top portion 30 is movably connectable to the bottom portion 32 of the clip 20 via a hinge portion 33. In this manner, the top portion 30 is movably connected to the bottom portion 32 of the clip 20 between the closed position (FIGS. 1-2 and 7-8) and the open position (FIGS. 3-5). In other embodiments, the top portion 30 is movably connectable to the bottom portion 32 of the clip 20 via other mechanical systems that allow the top portion 30 to move or swing open between the closed position (FIGS. 1-2 and 7-8) and the open position (FIGS. 3-5).

Referring to FIGS. 3-5, in some non-limiting embodiments, with the clip 20 in the open position in which the top portion 30 is spaced away from the bottom portion 32, an opening angle 54 between the top portion 30 and the bottom portion 32 is 35° or less. In this manner, the top portion 30 is spaced away from the bottom portion 32 a sufficient distance to allow a portion of a garment 12 to be securely received within the opening 56 formed between the top portion 30 and the bottom portion 32. Importantly, in the open position, the distance the top portion 30 is spaced away from the bottom portion 32 is controlled to allow a caregiver to position the garment 12 within the opening 56 formed between the top portion 30 and the bottom portion 32 and move the locking mechanism 22 into the first position to lock the clip 20 in the closed position, thereby securely attaching the clip 20 to the garment 12 using only one hand. This is important because the monitoring device 10 of the present disclosure only requires one hand of the caregiver to operate the monitoring device 10, thereby freeing the other hand of the caregiver to steady a patient and/or the garment 12 and/or be free to use for other activities needed in administering help to a patient.

Referring to FIG. 5, in some non-limiting embodiments, the top portion 30 of the clip 20 includes a rail 40 that is in communication with a portion of the locking mechanism 22 to allow a caregiver to easily open and close the monitoring device 10 using only one hand, as described in more detail below. In some non-limiting embodiments, the top portion 30 of the clip 20 includes two opposing rails 40.

Figure 9:
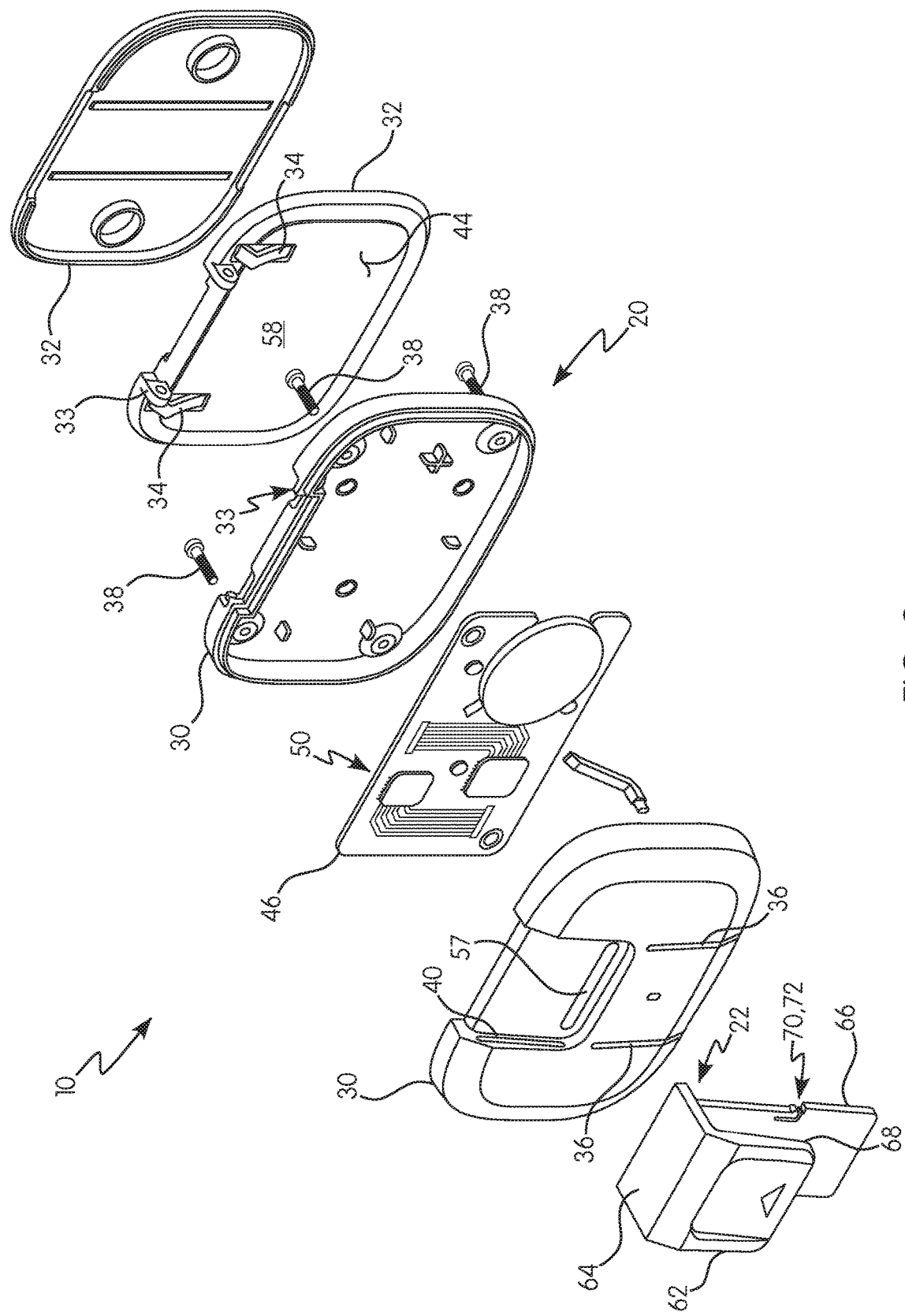
FIG. 9 is a first exploded, perspective view of a monitoring device in accordance with an embodiment of the present invention.
Figure 10:
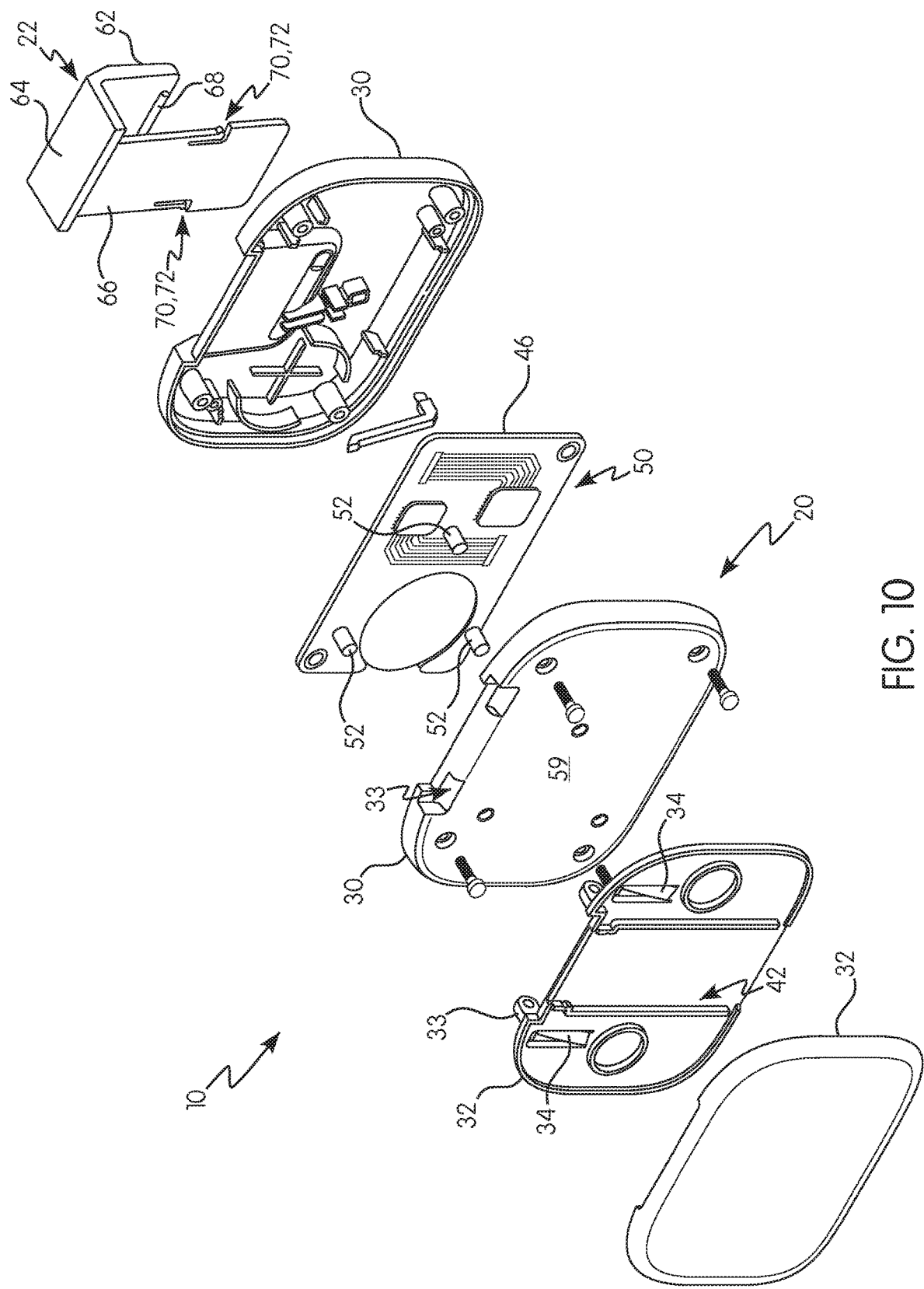
FIG. 10 is a second exploded, perspective view of a monitoring device in accordance with an embodiment of the present invention.

Referring to FIGS. 9 and 10, in an exemplary embodiment, the top portion 30 and the bottom portion 32 of the clip 20 may comprise two portions that are secured together using a plurality of fasteners 38.

Figure 11:
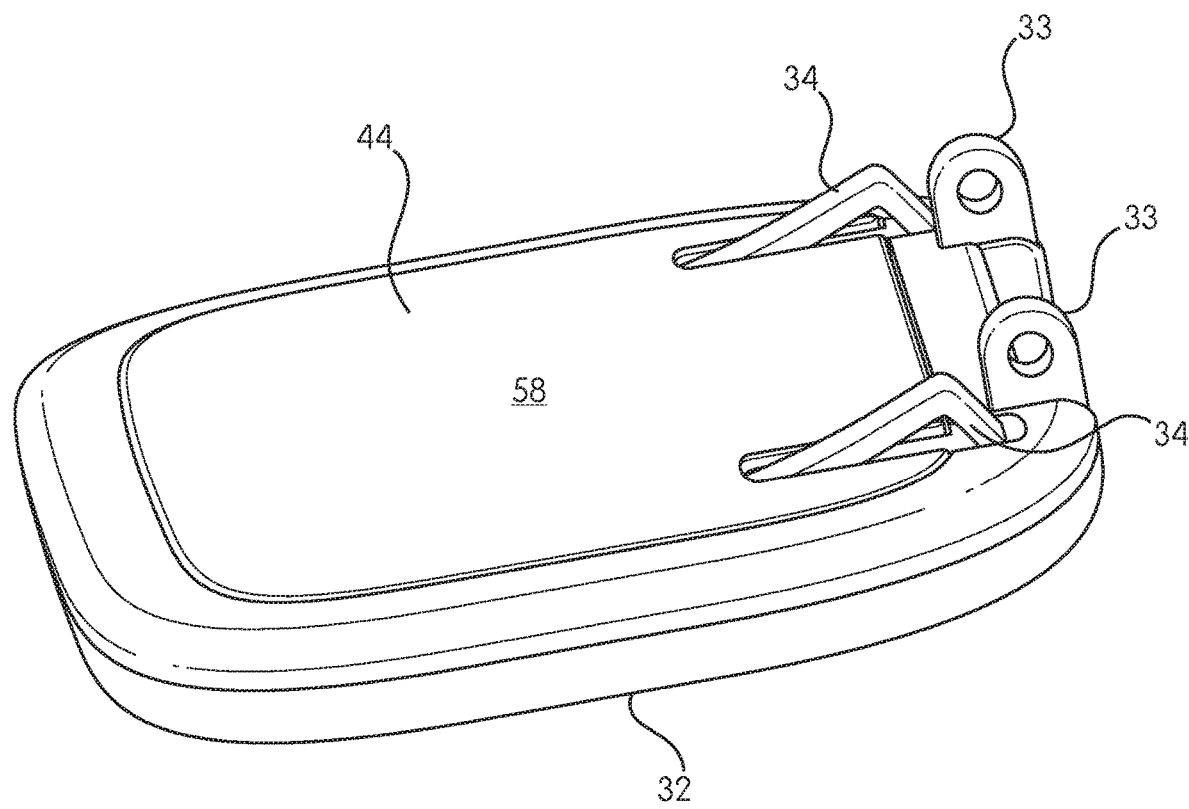
FIG. 11 is a top perspective view of a bottom portion of a clip including a resilient member in an undeformed position in accordance with an embodiment of the present invention.

The monitoring device 10 of the present disclosure also includes additional mechanisms to maintain the clip 20 in the open position, thereby making the monitoring device 10 easy to use with only one hand. For example, referring to FIGS. 9-14, in some non-limiting embodiments, the bottom portion 32 of the clip 20 includes a resilient member 34 that is transitionable between a deformed position (FIGS. 12 and 14) and an undeformed position (FIGS. 11 and 13). In one exemplary embodiment, the resilient member 34 is formed integrally with the bottom portion 32 of the clip 20.

Figure 12:
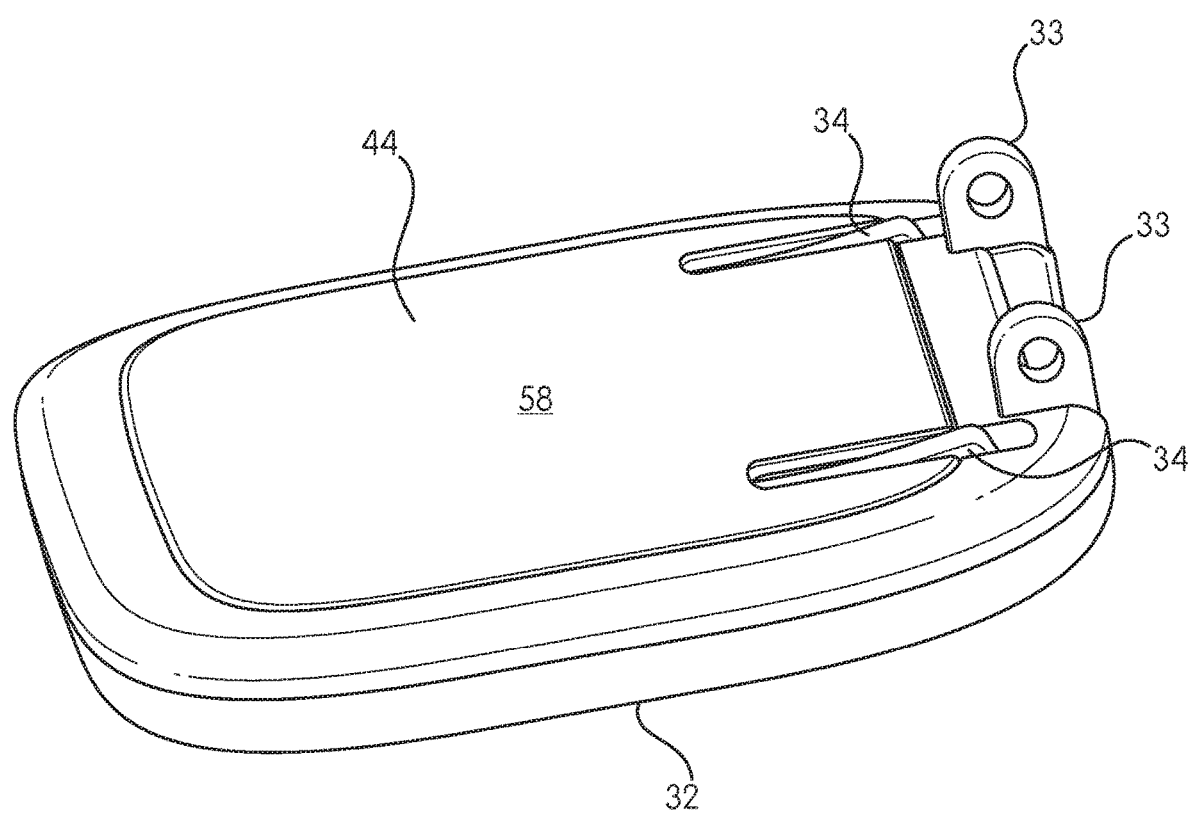
FIG. 12 is a top perspective view of a bottom portion of a clip including a resilient member in a deformed position in accordance with an embodiment of the present invention.
Figure 13:
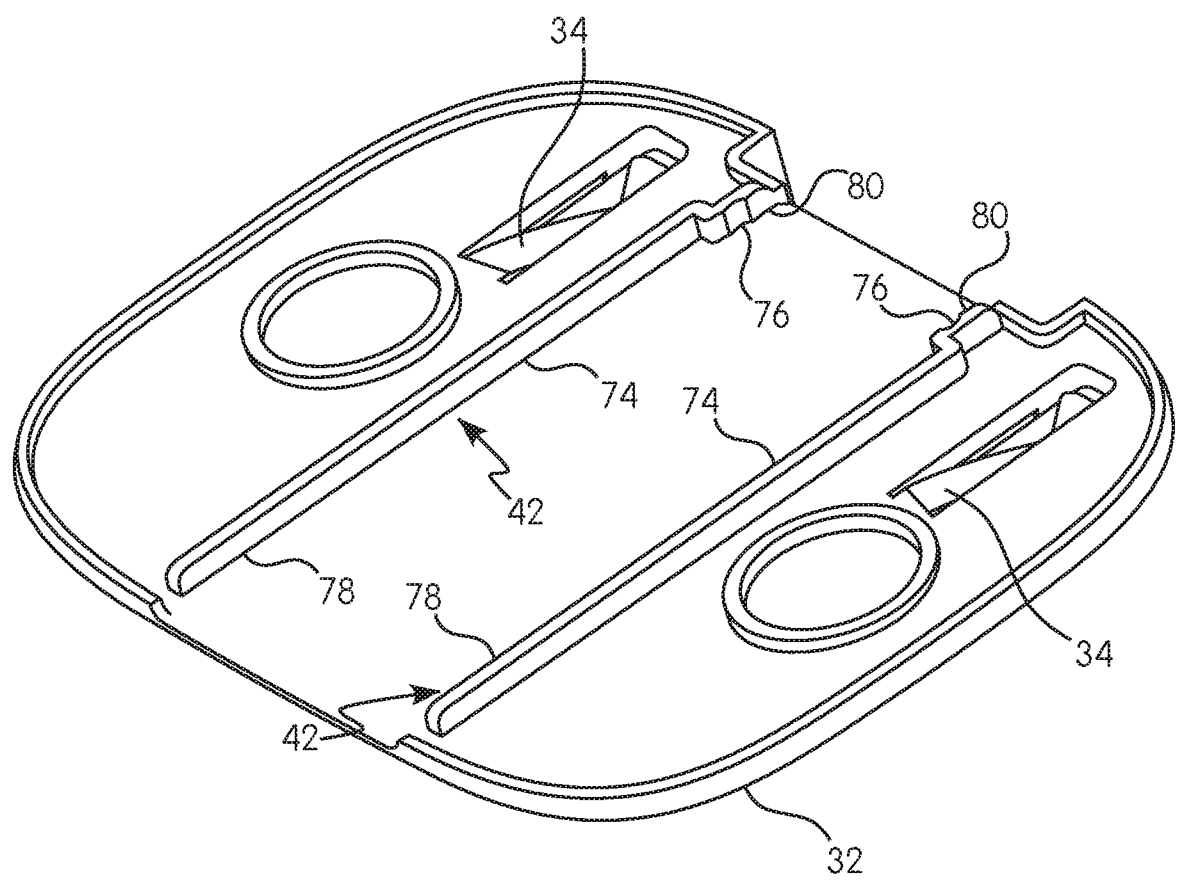
FIG. 13 is a bottom perspective view of a bottom portion of a clip including a resilient member in an undeformed position in accordance with an embodiment of the present invention.
Figure 14:
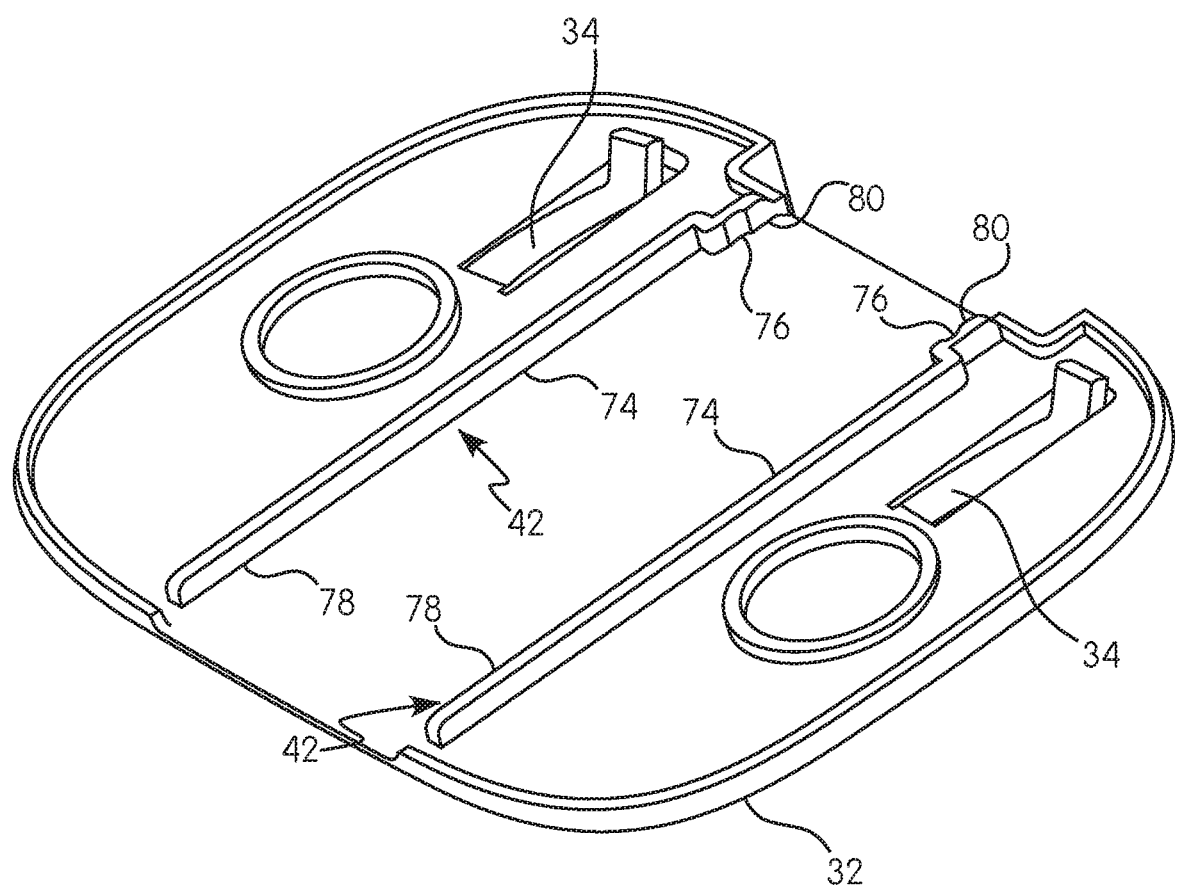
FIG. 14 is a bottom perspective view of a bottom portion of a clip including a resilient member in a deformed position in accordance with an embodiment of the present invention.

Referring to FIGS. 1-2 and 7-8, with the clip 20 in the closed position, the resilient member 34 is in the deformed position (FIGS. 12 and 14). Referring to FIGS. 3-5, with the clip 20 in the open position, the resilient member 34 is in the undeformed position (FIGS. 11 and 13).

Importantly, when the clip 20 moves from the open position to the closed position, as the top portion 30 of the clip 20 moves towards the bottom portion 32 of the clip 20, the top portion 30 contacts and forces the resilient member 34 to the deformed position. In other words, the top portion 30 compresses the resilient member 34 into the deformed position. In this manner, the resilient member 34 stores a force and when the clip 20 is subsequently moved from the closed position to the open position, the resilient member 34 exerts the stored force on the top portion 30 of the clip 20 as the resilient member 34 springs back into its undeformed position (FIGS. 11 and 13). Importantly, in this manner, the resilient member 34 helps to automatically open the clip 20. Also, with the clip 20 in the open position (FIGS. 3-5), and with the locking mechanism 22 in the second position, the clip 20 is locked in the open position by the resilient member 34 in the undeformed position exerting a force on the top portion 30 of the clip 20. This force exerted by the resilient member 34 automatically maintains the clip 20 in the open position. This enables a caregiver to not have to hold the clip 20 in an open position and enables one-handed operation of the monitoring device 10 of the present disclosure.

Referring to FIGS. 3 and 9, a portion of the clip 20 includes an elastomeric portion 44. In some non-limiting embodiments, a top surface 58 of the bottom portion 32 of the clip 20 includes an elastomeric portion 44. In another embodiment, a bottom surface 59 of the top portion 30 of the clip 20 includes an elastomeric portion 44. In other embodiments, a top surface 58 of the bottom portion 32 of the clip 20 includes an elastomeric portion 44 and a bottom surface 59 of the top portion 30 of the clip 20 includes an elastomeric portion 44.

The elastomeric portion 44 of the clip 20 provides a gripping surface that securely grips and holds a portion of the garment 12 within the clip 20. For example, with the clip 20 in the closed position and the clip 20 attached to the garment 12, the elastomeric portion 44 securely grips and holds the garment 12 within the clip 20. The elastomeric portion 44 provides an additional attachment mechanism in addition to the clip 20 and the locking mechanism 22 to ensure that a garment 12 is securely attached to the monitoring device 10.

Referring to FIGS. 9 and 10, the clip 20 includes a printed circuit board 46, a transmitter 50, and pins 52. In some non-limiting embodiments, the pins 52 are configured to determine moisture data associated with moisture in the sensors 48 (e.g., on the sensors, near the sensors, etc.) of the garment 12, and connect to the transmitter 50 configured to transmit the moisture data to a computer system comprising one or more processors (e.g., a central computer, a cloud computer, etc.).

For example, in one exemplary embodiment, the sensor 48 of the garment 12, the transmitter 50, and the computer system of the present disclosure comprises the system described in PCT Application PCT/US17/63042, filed Nov. 22, 2017, entitled "Monitoring Device, System, and Method for Incontinence Sensor Pad and Transmitter", the entire disclosure of which is hereby expressly incorporated herein by reference.

In some non-limiting embodiments, the transmitter 50 is included within the clip 20. In other embodiments, sensors 48 may be included in the garment 12 and the pins 52, attached to the printed circuit board 46 of the clip 20, extend through a portion of the top portion 30 into the opening 56 of the clip 20 to form connection points to both power and receive a signal from the sensors 48. For example, sensors may be attached to an interior portion of a garment 12. Although in FIG. 4 the pins 52 appear to have a flat head, it is contemplated that the heads of the pins 52 have teeth. For example, in some non-limiting embodiments, these pins 52 are crowned, e.g., the heads of the pins 52 have teeth allowing them to reliably penetrate through a top layer of non-woven textile on a portion of the garment 12 and penetrate into a sensor and/or sensor ink.

In one exemplary embodiment, the printed circuit board 46 may be contained within the top portion 30 of the clip 20. In another exemplary embodiment, the printed circuit board 46 may be contained within the bottom portion 32 of the clip 20. In one exemplary embodiment, the portion 30, 32 of the clip 20 that contains the printed circuit board 46 includes a removable access portion, such as a sliding tab (e.g., lock, enclosure, etc.). Such a removable access portion allows for easy access to the interior of the portion 30, 32 of the clip 20 that contains the printed circuit board 46. In this manner, tasks such as changing the printed circuit board 46, repair, changing the battery, or diagnostics can be accomplished easily and without taking the whole monitoring device 10 apart.

As described above, referring to FIGS. 1-5, the locking mechanism 22 is movably connected to the clip 20. In an exemplary embodiment, the locking mechanism 22 is transitionable between a first position (FIGS. 1-2 and 7-8) in which the locking mechanism 22 locks the clip 20 in a closed position and a second position (FIGS. 3-5) in which the clip 20 is in an open position.

Referring to FIGS. 1-8, in an exemplary embodiment, the locking mechanism 22 is movably connected to the clip 20, such that the locking mechanism 22 slides back and forth relative to the clip 20 between the first position (FIGS. 1-2 and 7-8) and the second position (FIGS. 3-5).

In an exemplary embodiment, as the locking mechanism transitions from the first position to the second position, the locking mechanism 22 helps to open the clip 20. For example, referring to FIG. 5, in some non-limiting embodiments, the locking mechanism 22 includes a protrusion 60 that is movable and/or slidable within the rail 40 of the clip 20. Referring to FIG. 5, in some non-limiting embodiments, the locking mechanism 22 includes two opposing protrusions 60 that are respectively received within the two opposing rails 40 on the top portion 30 of the clip 20. In this manner, the rail 40 of the clip 20 guides movement of the locking mechanism 22 relative to the clip 20 between the first position (FIGS. 1-2 and 7-8) and the second position (FIGS. 3-5).

Importantly, as the locking mechanism 22 transitions from the first position (FIGS. 1-2 and 7-8) to the second position (FIGS. 3-5), the protrusion 60 of the locking mechanism 22 within the rail 40 of the clip 20 exerts a force on the top portion 30 of the clip 20, such that the locking mechanism 22 helps to open the clip 20, i.e., the locking mechanism 22 helps to pull the top portion 30 of the clip 20 away from the bottom portion 32 of the clip 20. The protrusion 60 of the locking mechanism 22 exerts a force on the top portion 30 of the clip 20 via the engagement of the protrusion 60 within the rail 40 of the clip 20. In this manner, the locking mechanism 22 of the present disclosure allows a caregiver to easily open and close the monitoring device 10 using only one hand. This is important because the monitoring device 10 of the present disclosure only requires one hand of the caregiver to operate the monitoring device 10, thereby freeing the other hand of the caregiver to steady a patient and/or the garment 12 and/or be free to use for other activities needed in administering help to a patient.

In one exemplary embodiment, the locking mechanism 22 generally includes a top part 62, a side part 64, and a bottom part 66. Referring to FIGS. 9 and 10, in some non-limiting embodiments, the top part 62, the side part 64, and the bottom part 66 of the locking mechanism 22 form a generally J-shape.

In some non-limiting embodiments, the monitoring device 10 of the present disclosure includes a locking mechanism for maintaining and locking the locking mechanism 22 relative to the clip 20, with the locking mechanism 22 in the first position (FIGS. 1-2 and 7-8), i.e., with the locking mechanism 22 locking the clip 20 in the closed position. For example, in an exemplary embodiment, the top part 62 of the locking mechanism 22 includes a protruding rib 68 (FIGS. 9 and 10) and the top portion 30 of the clip 20 defines a groove 57 (FIGS. 3 and 5). In this manner, with the locking mechanism 22 in the first position (FIGS. 1-2 and 7-8), the protruding rib 68 of the locking mechanism 22 locks within the groove 57 of the grip 20 to maintain and lock the locking mechanism 22 relative to the clip 20, with the locking mechanism 22 in the first position (FIGS. 1-2 and 7-8), i.e., with the locking mechanism 22 locking the clip 20 in the closed position.

In some non-limiting embodiments, the monitoring device 10 of the present disclosure includes an additional locking mechanism for maintaining and locking the locking mechanism 22 relative to the clip 20, with the locking mechanism 22 in the second position (FIGS. 3-5) in which the clip 20 is in an open position.

For example, in an exemplary embodiment, the bottom part 66 of the locking mechanism 22 includes a link or second detent portion 70 movably connected to the bottom part 66 of the locking mechanism 22 and the bottom portion 32 of the clip 20, and with the locking mechanism 22 in the second position (FIGS. 3-5), the link or second detent portion 70 locks the locking mechanism 22 relative to the clip 20 so that movement of the locking mechanism 22 relative to the clip 20 is prevented.

In some non-limiting embodiments, the links 42, 70 comprise a detent system. For example, in some non-limiting embodiments, the second detent portion 70 of the locking mechanism 22 includes a resiliently deformable portion 72 and the first detent portion 42 of the clip 20 includes detent rails 74 on the bottom portion 32 of the clip 20 and locking apertures 76. In some non-limiting embodiments, the detent rails 74 include a first portion 78 and a second portion 80. The second portion 80 of the detent rails 74 defines the locking apertures 76. The second portion 80 of the detent rails 74 are spaced close together than the first portion 78 of the detent rails 74 so that the second portion 80 of the detent rails 74 compress the resiliently deformable portion 72 of the locking mechanism 22 as described below.

Figure 15:
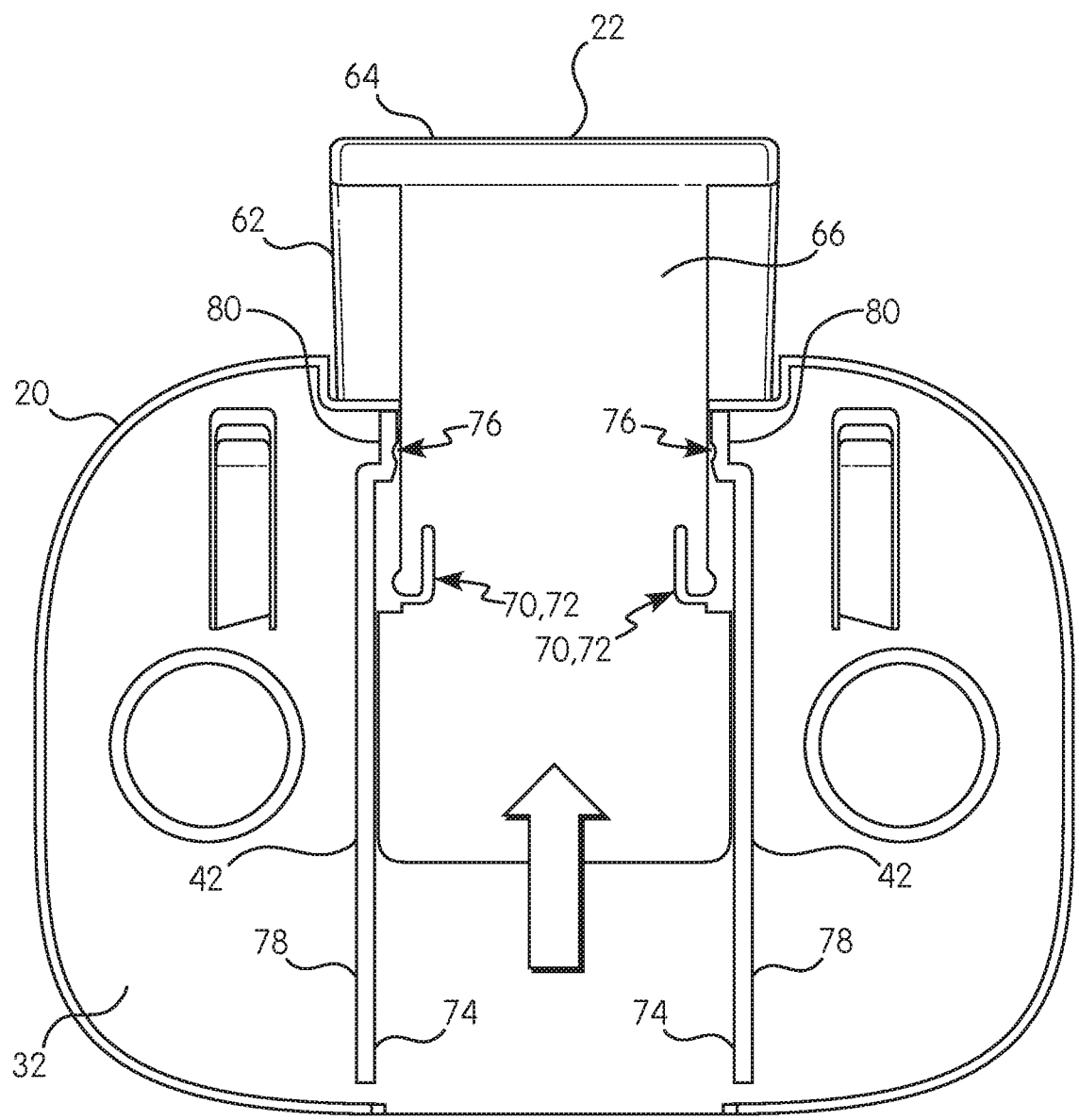
FIG. 15 is a perspective view of a detent system of a monitoring device in a first position in accordance with an embodiment of the present invention.
Figure 16:
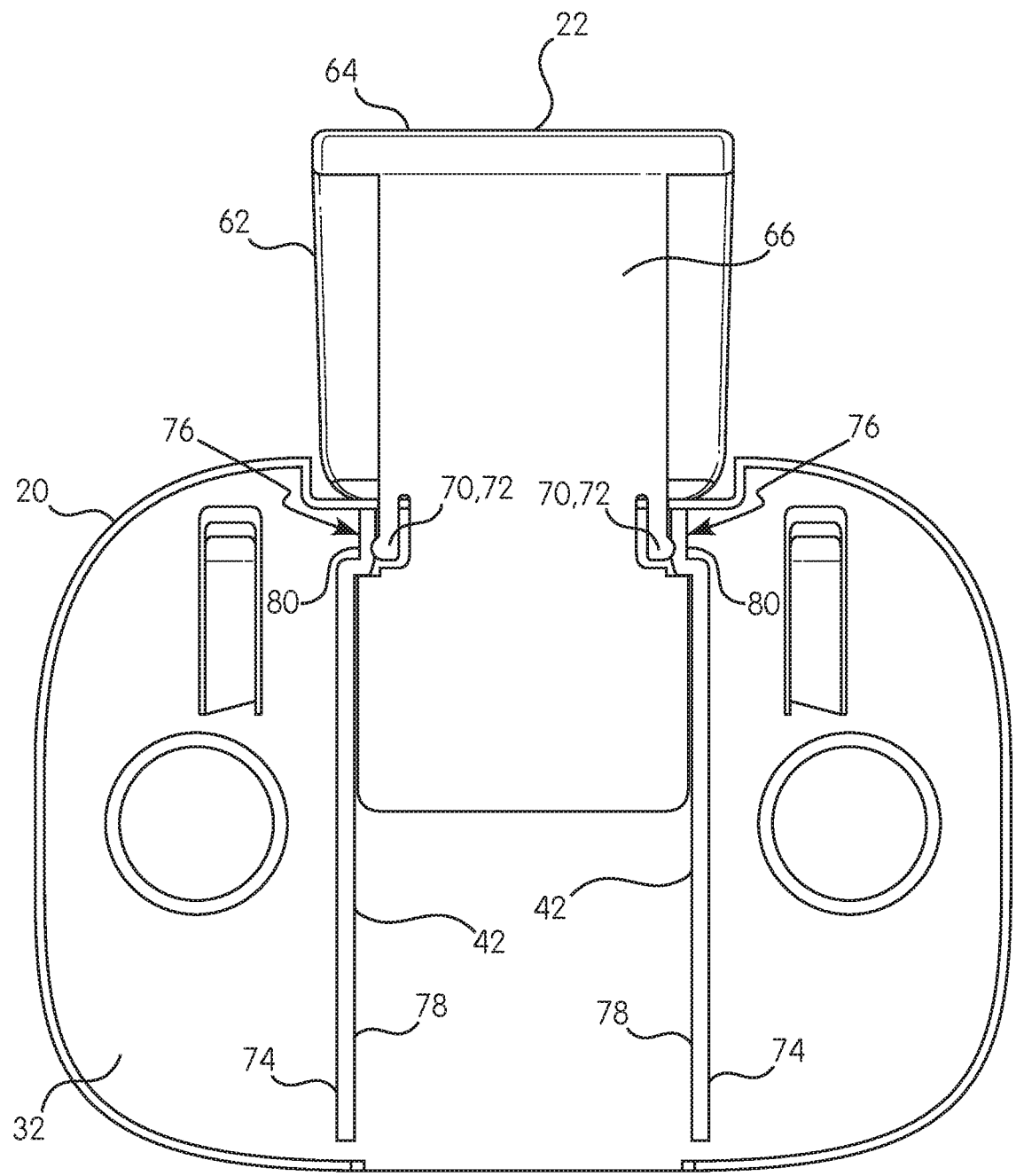
FIG. 16 is a perspective view of a detent system of a monitoring device in a second position in accordance with an embodiment of the present invention.

Referring to FIGS. 15 and 16, as the locking mechanism 22 transitions from the first position (FIGS. 1-2 and 7-8) to the second position (FIGS. 3-5 and 16), the deformable portion 72 of the second detent portion 70 of the locking mechanism 22 travels between the first portion 78 of the detent rails 74. When the deformable portion 72 of the locking mechanism 22 reaches the beginning of the second portion 80 of the detent rails 74, the second portion 80 of the detent rails 74 contacts and deforms the deformable portion 72 of the locking mechanism 22 inwards, thereby storing a force. The locking mechanism 22 continues to transition from the first position (FIGS. 1-2 and 7-8) to the second position (FIGS. 3-5 and 16) until the deformable portion 72 of the locking mechanism 22 reaches the locking apertures 76 of the second portion 80 of the first detent portion 42 of the clip 20. At this point, the energy stored within the deformable portion 72 of the locking mechanism 22 is released and the deformable portion 72 snaps into the locking apertures 76, thereby locking the locking mechanism 22 relative to the clip 20 so that movement of the locking mechanism 22 relative to the clip 20 is prevented with the locking mechanism 22 in the second position (FIGS. 3-5 and 16) in which the clip 20 is in an open position. This mechanism also helps to allow a caregiver to easily use the monitoring device 10 using only one hand.

Referring to FIG. 3, when a caregiver is aligning the monitoring device 10 relative to a garment 12 before securely attaching the monitoring device 10 to the garment 12, a caregiver only needs one hand because the locking mechanism 22 is securely maintained in the second position. If the top portion 30 and the bottom portion 32 of the clip were not locked into position and were freely moving between each other, it would take a caregiver two hands just to maintain the clip in an open position. The present disclosure allowing for one-handed use is important because the monitoring device 10 of the present disclosure only requires one hand of the caregiver to operate the monitoring device 10, thereby freeing the other hand of the caregiver to steady a patient and/or the garment 12 and/or be free to use for other activities needed in administering help to a patient.

In some non-limiting embodiments, the locking mechanism 22 comprises a polymer component molded over a metal component. In other embodiments, the locking mechanism 22 may comprise other materials and/or combinations of materials that provide a sufficient strength to lock the clip 20 in the closed position (FIGS. 1-2 and 7-8).

Advantageously, the monitoring device 10 of the present disclosure may be part of a monitoring system. For example, a monitoring device 10 of the present disclosure is reusable and can be used an unlimited amount of times with an unlimited amount of disposable garments 12. Thus, a single monitoring device 10 of the present disclosure can be used with a first garment 12 to detect wetness in the first garment 12. After use, the first garment 12 is disposed of and the monitoring device 10 of the present disclosure can be reused with a second garment 12.

Referring to FIGS. 1-8, use of a monitoring device 10 of the present disclosure will now be described.

Referring to FIG. 3, with the locking mechanism 22 in the second position in which the clip 20 is in an open position, and with the locking mechanism 22 locked relative to the clip 20 so that movement of the locking mechanism 22 relative to the clip 20 is prevented using links 42, 70, as described above, a caregiver is able to use only one hand to align and maneuver the monitoring device 10 relative to a garment 12. In some non-limiting embodiments, a caregiver aligns the guide lines 36 located on the top portion 30 of the clip 20 with guide lines 14 on the garment 12 to properly position the monitoring device 10 relative to the garment 12 before securely attaching the monitoring device 10 to the garment 12. These guide lines 14, 36 ensure that the monitoring device 10 is secured to the garment 12 in a proper position that will allow sensors 48 of the system to be aligned with pins 52 of the clip 20 so that the transmitter 50 of the monitoring device 10 is in communication with the sensors 48 that determine moisture data associated with moisture in the garment 12. In this manner, the transmitter 50 of the monitoring device 10 is able to connect to the sensor 48 and transmit the moisture data to a computer system comprising one or more processors.

Referring to FIG. 3, with the monitoring device 10 properly aligned with the garment 12, the caregiver is able to position a portion of the garment 12 within the opening 56 of the monitoring device 10, and then using only one hand slide, the locking mechanism 22 into the first position (FIGS. 1-2 and 7-8) in which the locking mechanism 22 locks the clip 20 in the closed position to securely attach the monitoring device 10 to the garment 12.

In a first configuration, referring to FIG. 7, the monitoring device 10 is secured to a portion of the garment 12 that has been folded over. In such a configuration, the folded over portion of the garment 12 provides an increased thickness portion of the garment 12 that is secured within the clip 20 of the monitoring device 10. In this manner, the thicker portion of the garment 12 can lead to a more secure attachment between the monitoring device 10 and the garment 12.

In a second configuration, referring to FIG. 8, the monitoring device 10 is secured to the inside layer of a portion of the garment 12 that has been folded over. In such a configuration, the monitoring device 10 is secured to the garment 12 so that the monitoring device 10 does not contact any portion of a patient. In this manner, the monitoring device 10 is secured between two layers of the garment 12 and avoids contacting any skin surfaces of a patient. Both of the configurations of FIGS. 7 and 8 lead to a secure attachment between the monitoring device 10 and a garment 12.

With the monitoring device 10 properly attached to a garment 12, the monitoring device 10 is able to detect wetness in a garment. For example, in one exemplary embodiment, the sensor 48, the transmitter 50, and the computer system of the present disclosure for detecting moisture data and transmitting the moisture data comprise a system described in PCT Application PCT/US17/63042, filed Nov. 22, 2017, entitled "Monitoring Device, System, and Method for Incontinence Sensor Pad and Transmitter", the entire disclosure of which is hereby expressly incorporated herein by reference.

After moisture data is determined and transmitted to a caregiver, the caregiver is able to remove the monitoring device 10 of the present disclosure using only one hand, as described above, and then the garment 12 is disposed of. As described above, the monitoring device 10 of the present disclosure is then reusable with any number of additional garments 12.

The monitoring device 10 of the present disclosure provides a patient incontinence monitoring system for electronically detecting the presence of moisture in a patient care or home care environment. It can send a detection of moisture across a network to a third-party device (e.g., a computer, a remote pad, a smartphone, a cloud) for enabling the remote collection and analysis of incontinence data. This detection can also be used by a third-party device, such as a monitoring system, to determine patterns and/or alert a caregiver associated with an incontinence event.

Figure 17:
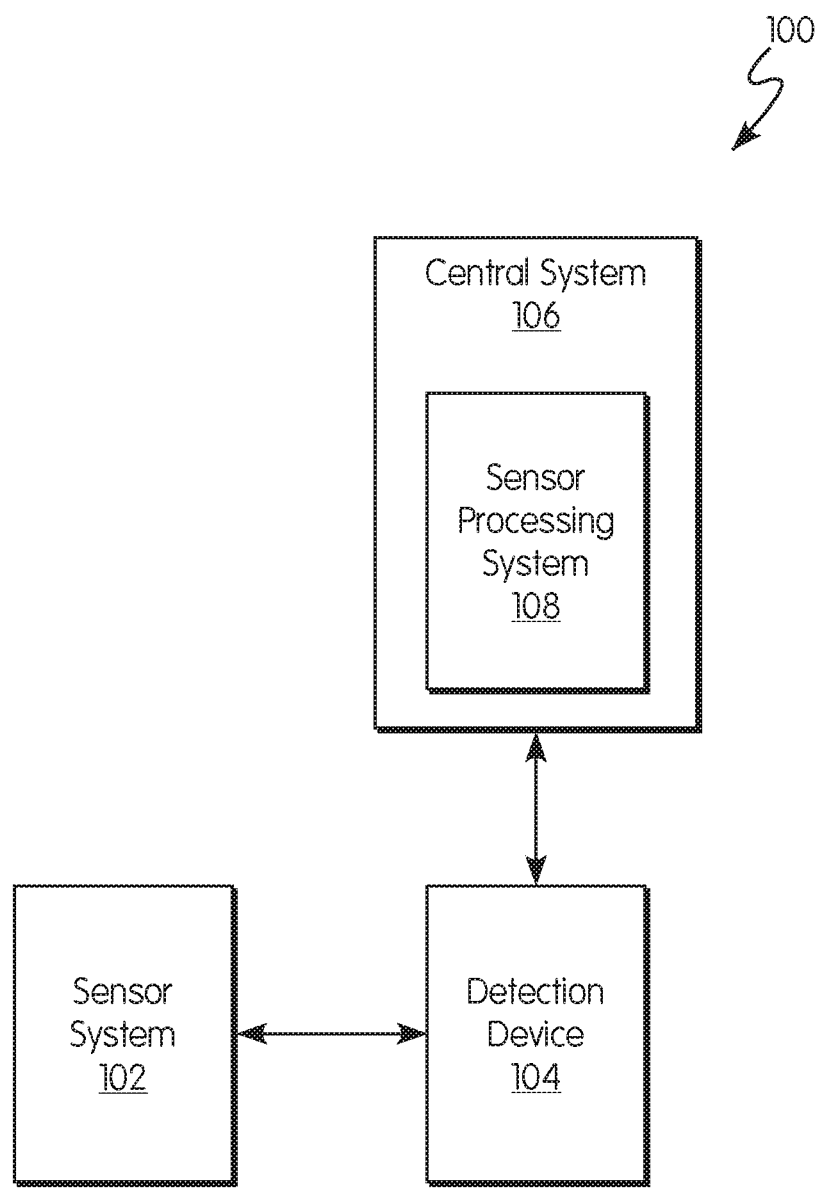
FIG. 17 is a first diagram showing a monitoring device and patient incontinence monitoring system in accordance with an embodiment of the present invention.
Figure 18:
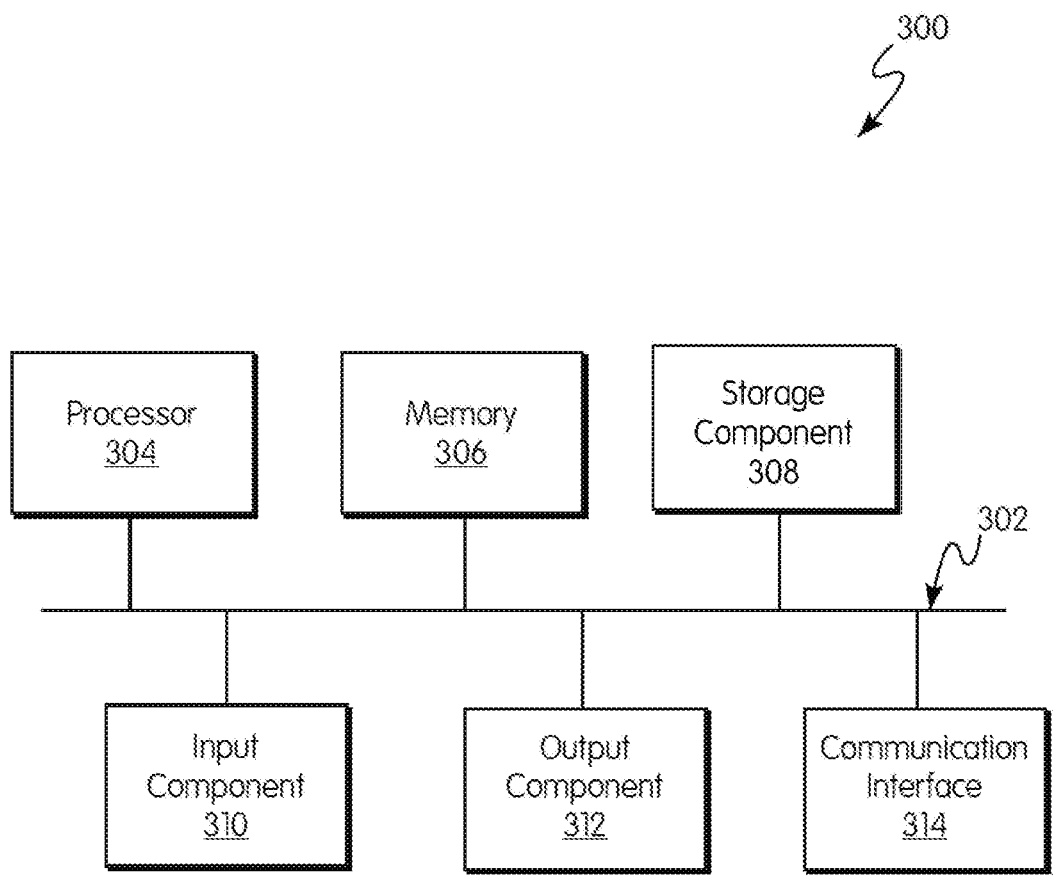
FIG. 18 is a second diagram showing a monitoring device and patient incontinence monitoring system in accordance with an embodiment of the present invention.
Figure 19:
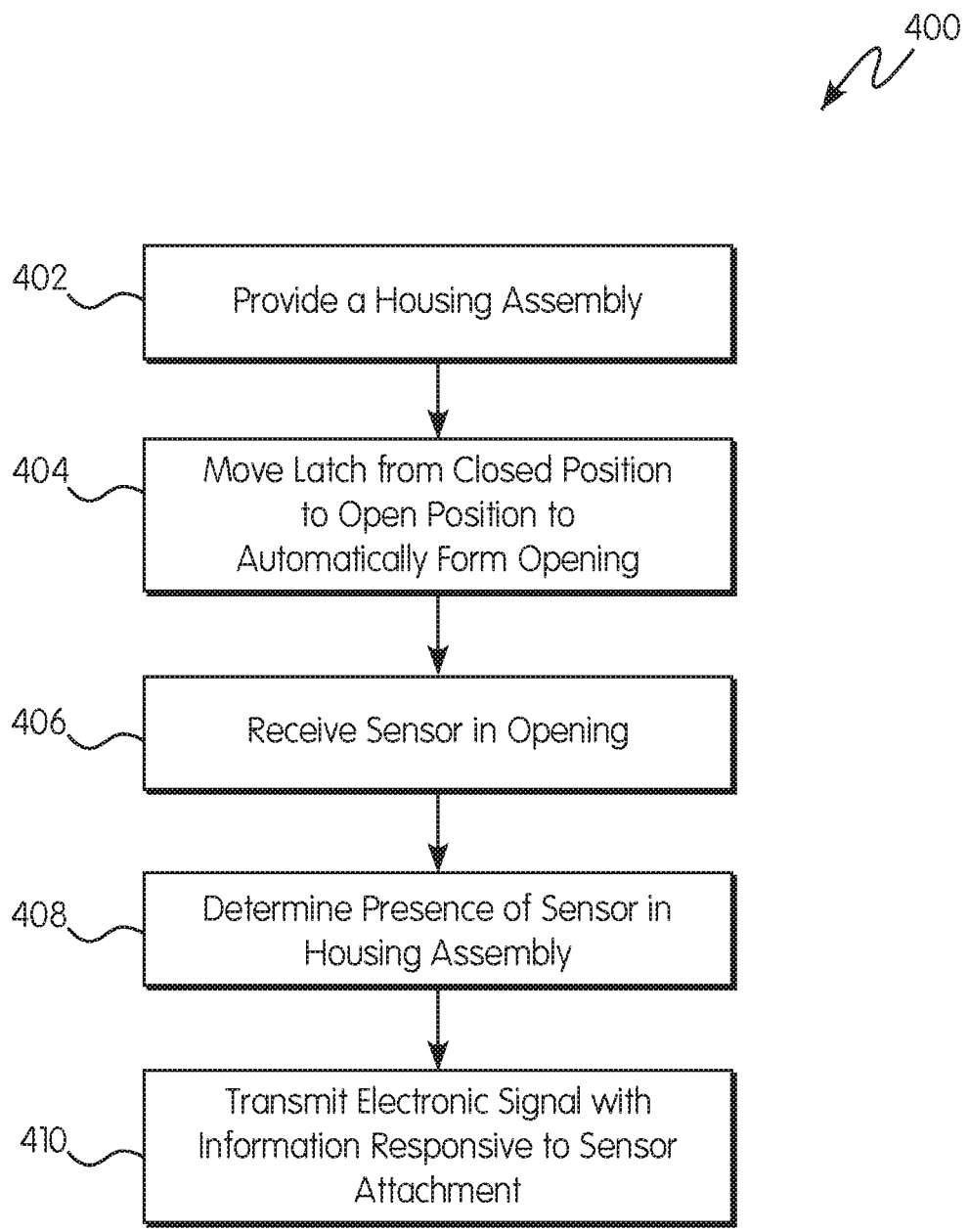
FIG. 19 is a flow chart showing a monitoring device and patient incontinence monitoring system in accordance with an embodiment of the present invention.

Furthermore, diagrams and/or flow charts of a system and/or device of the present disclosure are illustrated in FIGS. 17-19. Referring to FIG. 17, a system or device 100 includes a sensor system 102 configured to determine moisture data associated with moisture in a garment 12, a detection device 104, a central system 106, a sensor processing system 108, and a transmitter 50 configured to connect to the sensor 102 and transmit the moisture data to a computer system comprising one or more processors.

In an exemplary embodiment, each of the layers of a multi-layer location-based sensor pad may be made of an absorbent material. The sensor pad may be placed on a flat surface (e.g., a patient bed, a patient chair) and may also be placed on surfaces not flat, where the pad can take the shape of the surface. The pad can also be wrapped around a patient's body or configured to provide sufficient coverage for incontinence detection. The sensor pad may be placed inside a wearable unit and may take the shape of the wearable unit. In one exemplary embodiment, a sensor and/or sensor pad may be attached to an interior of a garment. For example, a sensor may be attached to an interior of a garment, such as, for example, briefs, diapers, pull-ups, or other wearable garments. In such embodiments, a sensor may be printed directly into a wearable garment with a tail coming out of a portion of the garment to facilitate the attachment with a transmitter.

Referring to FIG. 18, a diagram of non-limiting embodiment of components of one or more monitoring devices and/or monitoring systems of the present disclosure is illustrated.

In one exemplary embodiment, FIG. 18 is a diagram of example components of a monitoring device 300 (e.g., monitoring system, etc.) of the present disclosure. Monitoring device 300 may correspond to one or more devices of a patient incontinence monitoring system, one or more monitoring devices of the present disclosure that may include at least one monitoring device 300 and/or at least one component of monitoring device 300. Referring to FIG. 18, the monitoring device 300 may include bus 302, processor 304, memory 306, storage component 308, input component 310, output component 312, and communication interface 314.

Bus 302 may include a component that permits communication among the components of monitoring device 300. In some non-limiting embodiments, processor 304 may be implemented in hardware, firmware, or a combination of hardware and software. For example, processor 304 may include a processor (e.g., a central processing unit (CPU), a graphics processing unit (GPU), an accelerated processing unit (APU), etc.), a microprocessor, a digital signal processor (DSP), and/or any processing component (e.g., a fieldprogrammable gate array (FPGA), an application-specific integrated circuit (ASIC), etc.) that can be programmed to perform a function. Memory 306 may include a random access memory (RAM), a read only memory (ROM), and/or another type of dynamic or static storage device (e.g., flash memory, magnetic memory, optical memory, etc.) that stores information and/or instructions for use by processor 304.

Storage component 308 may store information and/or software related to the operation and use of monitoring device 300. For example, storage component 308 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 310 may include a component that permits monitoring device 300 to receive information, such as via user input (e.g., a touch screen display, a keyboard, a keypad, a mouse, a button, a switch, a microphone, etc.). Additionally, or alternatively, input component 310 may include a sensor for sensing information (e.g., a global positioning system (GPS) component, an accelerometer, a gyroscope, an actuator, etc.). Output component 312 may include a component that provides output information from monitoring device 300 (e.g., a display, a speaker, one or more light-emitting diodes (LEDs), etc.).

Communication interface 314 may include a transceiver-like component (e.g., a transceiver, a separate receiver and transmitter, etc.) that enables monitoring device 300 to communicate with other devices, such as via a wired connection, a wireless connection, or a combination of wired and wireless connections. Communication interface 314 may permit monitoring device 300 to receive information from another device and/or provide information to another device. For example, communication interface 314 may include an Ethernet interface, an optical interface, a coaxial interface, an infrared interface, a radio frequency (RF) interface, a universal serial bus (USB) interface, a Wi-Fi interface, a cellular network interface, and/or the like.

Monitoring device 300 may perform one or more processes described herein. Monitoring device 300 may perform these processes based on processor 304 executing software instructions stored by a computer-readable medium, such as memory 306 and/or storage component 308. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 306 and/or storage component 308 from another computer-readable medium or from another device via communication interface 314. When executed, software instructions stored in memory 306 and/or storage component 308 may cause processor 304 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software.

The number and arrangement of components shown in FIG. 18 are provided as an example. In some non-limiting embodiments, monitoring device 300 may include additional components, fewer components, different components, or differently arranged components than those shown in FIG. 18. Additionally, or alternatively, a set of components (e.g., one or more components) of monitoring device 300 may perform one or more functions described as being performed by another set of components of monitoring device 300.

Referring to FIG. 19, in some non-limiting embodiments, a computer-implemented monitoring method 400 includes steps 402, 404, 406, 408, 410 for patient care use in a patient incontinence monitoring system. As shown in FIG. 19, at step 402, monitoring method 400 includes providing a housing assembly. For example, monitoring method 400 includes a housing assembly for detecting wetness in a garment that includes a clip 20 and a locking mechanism 22 (e.g., a latch, etc.). The clip 20 and locking mechanism 22 provide a mechanism for removably attaching the monitoring device 10 to a garment 12. The monitoring device 10 of the present disclosure is compatible with any type of under garment with sensors. For example, a sensor pad may be used in a healthcare facility for detection of wetness associated with a patient.

As shown in FIG. 19, at step 404, monitoring method 400 includes moving a latch from a closed position to an open position to automatically form an opening. For example, monitoring method 400 includes a locking mechanism 22 (e.g., a latch) providing transitions from a first position to a second position. In some non-limiting embodiments, monitoring method 400 includes moving a latch (e.g., a deformable portion 72 of a second detent portion 70 of the locking mechanism 22, etc.) between portions of detent rail 74. For example, monitoring method 400 includes moving a latch to transition from a first position to a second position in a location where a deformable portion 72 of a locking mechanism 22 reaches the locking apertures 76 of the second portion 80 of the first detent portion 42 of the clip 20. For example, monitoring method 400 includes moving a latch until the energy stored within the deformable portion 72 of the locking mechanism 22 is released and the deformable portion 72 snaps into the locking apertures 76, thereby locking the locking mechanism 22 relative to the clip 20 so that movement of the locking mechanism 22 relative to the clip 20 is prevented with the locking mechanism 22 in the second position in which the clip 20 is in an open position.

As shown in FIG. 19, at step 406, monitoring method 400 includes receiving a sensor in an opening. For example, the monitoring method 400 includes receiving a sensor (e.g., a sensor pad, a sensor brief, etc.) of a garment in the monitoring device. For example, monitoring device 10 receives sensors 48 attached to an interior portion of a garment 12. In an example, monitoring method 400 includes receiving a sensor printed directly into a wearable garment providing a tail coming out of a portion of the garment. In some non-limiting embodiments, monitoring method 400 includes receiving a sensor (e.g., an end of a sensor, a portion of a sensor, a connector of a sensor, etc.) in an opening of the monitoring device 10. For example, a sensor is received in an opening of the monitoring device where pins 52, extend through a portion into the opening 56 of the monitoring device to form a connection at a point (e.g., location, etc.) when paired with a sensor. In some non-limiting embodiments, monitoring method 400 includes receiving a sensor in an opening of the monitoring device 10 to both power and receive a signal from the sensors 48.

As shown in FIG. 19, at step 408, monitoring method 400 includes determining a presence of a sensor in a housing assembly. For example, monitoring method 400 includes determining a presence of a sensor in a housing assembly (e.g., a monitoring device 10, etc.) to secure a portion of the garment 12 (e.g., a portion that has been folded over, a top portion of a garment, a portion having sensors, a portion having a tail of a sensor, etc.) For example, monitoring method 400 includes attaching a housing assembly to a folded portion of a garment 12, including an increased thickness portion. For example, monitoring method 400 includes securing a folder portion of the garment 12 within a clip 20 of the monitoring device 10. In some non-limiting embodiments, monitoring method 400 includes providing a secure attachment between the monitoring device 10 and the garment 12, and pins 52, attached to a printed circuit board 46 of a clip 20, extending into sensors 48 to both power and receive a signal from the sensors 48.

As shown in FIG. 19, at step 410, monitoring method 400 includes transmitting an electronic signal with information responsive to a sensor attachment. For example, monitoring method 400 includes a monitoring device 10 for electronically detecting a presence of moisture (e.g., a location, a quantity, a chemical composition, etc.) in a patient care or home care environment. In some non-limiting embodiments, monitoring device 10 can provide a detection of moisture across a network to a third-party device (e.g., a computer, a remote pad, a smartphone, a cloud) for enabling the remote collection and analysis of incontinence data. This detection can also be used by a third-party device, such as a monitoring system, to determine patterns and/or alert a caregiver associated with an incontinence event.

The monitoring device 10 of the present disclosure is directed to a monitoring device for detecting wetness in a garment. The monitoring device of the present disclosure includes a locking mechanism that slides back and forth relative to a clip that is removably attachable to a garment between a first position in which the locking mechanism locks the clip in a closed position and a second position in which the clip is in an open position. As the locking mechanism transitions from the first position to the second position, the locking mechanism opens the clip.

Advantageously, the monitoring device of the present disclosure allows a caregiver to align and secure the monitoring device to a garment using only one hand.

While this disclosure has been described as having exemplary designs, the present disclosure can be further modified within the spirit and scope of this disclosure. This application is, therefore, intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A monitoring device for detecting wetness in a garment, comprising:
   a clip removably attachable to the garment, wherein the clip comprises a top portion and a bottom portion and the bottom portion of the clip includes a resilient member transitionable between a deformed position and an undeformed position; and
   a locking mechanism movably connected to the clip, the locking mechanism transitionable between a first position in which the locking mechanism locks the clip in a closed position and a second position in which the clip is in an open position;
   wherein, with the locking mechanism in the second position, the clip is locked in the open position by the resilient member in the undeformed position exerting a force on the top portion of the clip.

2. The monitoring device of claim 1, wherein the locking mechanism slides back and forth relative to the clip between the first position and the second position.

3. The monitoring device of claim 1, wherein as the locking mechanism transitions from the first position to the second position, the locking mechanism opens the clip.

4. The monitoring device of claim 1, wherein, with the clip in the closed position, the resilient member is in the deformed position, and with the clip in the open position, the resilient member is in the undeformed position.

5. The monitoring device of claim 1, wherein the clip comprises an elastomeric portion, and with the clip in the closed position and the clip attached to the garment, the elastomeric portion grips the garment.

6. The monitoring device of claim 1, wherein, with the clip in the open position, an opening angle between the top portion and the bottom portion is 35 degrees or less.

7. The monitoring device of claim 1, wherein the locking mechanism comprises a polymer component molded over a metal component.

8. The monitoring device of claim 1, wherein the clip further comprises: one or more pins configured to determine moisture data associated with moisture in the garment; and a transmitter configured to receive moisture data associated with a sensor in the garment and transmit the moisture data to a computer system comprising one or more processors.

9. The monitoring device of claim 1, wherein the clip further comprises: a printed circuit board; and a plurality of pins in communication with the printed circuit board, a portion of the plurality of pins extending through a portion of the clip, wherein, with the clip attached to the garment, the printed circuit board is in communication with the garment via the plurality of pins.

10. A monitoring device for detecting wetness in a garment, comprising:
    a clip removably attachable to the garment, wherein the clip comprises a top portion and a bottom portion; and
    a locking mechanism movably connected to the bottom portion of the clip, the locking mechanism transitionable between a first position in which the locking mechanism locks the clip in a closed position and a second position in which the clip is in an open position;
    wherein the top portion of the clip includes a rail and the locking mechanism includes a protrusion engaged within the rail during movement between the first position and the second position, wherein the rail guides movement of the locking mechanism relative to the clip between the first position and the second position.

11. The monitoring device of claim 10, wherein as the locking mechanism transitions from the first position to the second position, the protrusion within the rail exerts a force on the top portion of the clip such that the locking mechanism opens the clip.

12. The monitoring device of claim 10, wherein the locking mechanism comprises a top part, a side part, and a bottom part.

13. The monitoring device of claim 12, wherein the top part, the side part, and the bottom part form a generally J-shape.

14. The monitoring device of claim 12, wherein the top part of the locking mechanism includes a protruding rib and the top portion of the clip defines a groove, and with the locking mechanism in the first position, the protruding rib locks within the groove.

15. The monitoring device of claim 12, wherein the bottom part of the locking mechanism includes a link movably connected to the bottom part of the locking mechanism and the bottom portion of the clip, and with the locking mechanism in the second position, the link locks the locking mechanism relative to the clip so that movement of the locking mechanism relative to the clip is prevented.

16. The monitoring device of claim 15, wherein the link comprises a detent system.

17. A monitoring system, comprising:
   a monitoring device for detecting wetness in a garment, comprising:
      a clip including a top portion and a bottom portion, where the bottom portion of the clip includes a resilient member transitionable between a deformed position and an undeformed position; and
      a locking mechanism movably connected to the clip, the locking mechanism transitionable between a first position in which the locking mechanism locks the clip in a closed position and a second position in which the clip is in an open position;
      wherein, with the locking mechanism in the second position, the clip is locked in the open position by the resilient member in the undeformed position exerting a force on the top portion of the clip;
   the monitoring system further comprising:
      a first garment; and
      a second garment;
      wherein the clip of the monitoring device is removably attachable to the first garment and the second garment.

18. The monitoring system of claim 17, wherein the monitoring device is reusable and the first garment and the second garment are disposable.

19. The monitoring system of claim 17, wherein as the locking mechanism transitions from the first position to the second position, the locking mechanism opens the clip.

20. A monitoring system, comprising:
   a monitoring device for detecting wetness in a garment, comprising:
      a clip including a top portion and a bottom portion; and
      a locking mechanism movably connected to the bottom portion of the clip, the locking mechanism transitionable between a first position in which the locking mechanism locks the clip in a closed position and a second position in which the clip is in an open position;
      wherein the top portion of the clip includes a rail and the locking mechanism includes a protrusion engaged within the rail during movement between the first position and the second position, wherein the rail guides movement of the locking mechanism relative to the clip between the first position and the second position;
   the monitoring system further comprising:
      a first garment; and
      a second garment;
      wherein the clip of the monitoring device is removably attachable to the first garment and the second garment.

21. The monitoring system of claim 20, wherein as the locking mechanism transitions from the first position to the second position, the protrusion within the rail exerts a force on the top portion of the clip such that the locking mechanism opens the clip.

22. The monitoring system of claim 20, wherein the monitoring device is reusable and the first garment and the second garment are disposable.

23. The monitoring system of claim 20, wherein the bottom portion of the clip includes a resilient member transitionable between a deformed position and an undeformed position and, with the locking mechanism in the second position, the clip is locked in the open position by the resilient member in the undeformed position exerting a force on the top portion of the clip.

* * * * *